(12) United States Patent
Agrawal et al.

(10) Patent No.: US 11,402,153 B2
(45) Date of Patent: Aug. 2, 2022

(54) SYSTEMS AND PROCESSES FOR UPGRADING NATURAL GAS LIQUIDS FROM SHALE GAS

(71) Applicant: PURDUE RESEARCH FOUNDATION, West Lafayette, IN (US)

(72) Inventors: Rakesh Agrawal, West Lafayette, IN (US); Zewei Chen, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 104 days.

(21) Appl. No.: 17/072,555

(22) Filed: Oct. 16, 2020

(65) Prior Publication Data
US 2021/0116172 A1 Apr. 22, 2021

Related U.S. Application Data

(60) Provisional application No. 62/923,135, filed on Oct. 18, 2019.

(51) Int. Cl.
*C10L 3/00* (2006.01)
*F25J 1/00* (2006.01)
*C10L 3/10* (2006.01)

(52) U.S. Cl.
CPC ............. *F25J 1/0022* (2013.01); *C10L 3/101* (2013.01); *C10L 2290/541* (2013.01); *F25J 2200/78* (2013.01); *F25J 2205/02* (2013.01); *F25J 2205/50* (2013.01); *F25J 2210/62* (2013.01); *F25J 2215/04* (2013.01); *F25J 2215/60* (2013.01)

(58) Field of Classification Search
CPC .......... C07C 11/04; C07C 11/06; C07C 2/76; C07C 11/02; C07C 2/06; C07C 5/32; C10G 21/04; C10G 50/00; C10G 55/02; C10G 57/02; C10G 5/04; C10L 2290/10; C10L 2290/541; C10L 3/101; C10L 3/12
See application file for complete search history.

(56) References Cited

U.S. PATENT DOCUMENTS

2020/0308088 A1* 10/2020 Agrawal ................ C10G 11/00

* cited by examiner

*Primary Examiner* — Sharon Pregler
(74) *Attorney, Agent, or Firm* — Edmonds & Cmaidalka, P.C.

(57) ABSTRACT

Systems and processes for upgrading natural gas liquids (NGL). A natural gas, preferably a shale gas, comprising methane and one or more natural gas liquids can be converted to one or more liquid hydrocarbons. Methane can be separated from the one or more liquid hydrocarbons using a liquid absorbent to provide a first separated stream comprising the methane from the converted stream and a second separated stream comprising the one or more liquid hydrocarbons from the converted stream. At least a portion of the one or more liquid hydrocarbons can be recycled as the liquid absorbent.

20 Claims, 25 Drawing Sheets

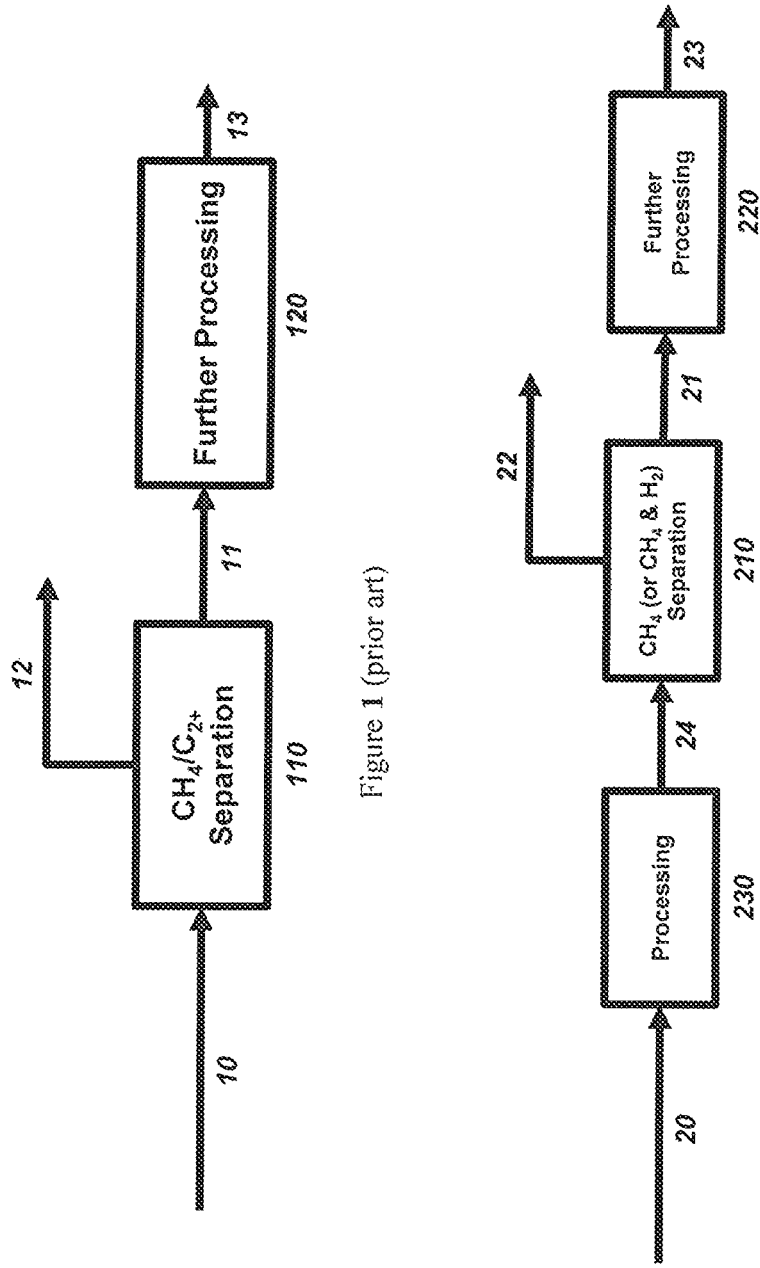

SYSTEMS AND PROCESSES FOR UPGRADING NATURAL GAS LIQUIDS FROM SHALE GAS

CROSS-REFERENCE TO RELATED APPLICATION

This application claims priority to U.S. Provisional Patent Application No. 62/923,135, filed on Oct. 18, 2019, which is incorporated by reference herein.

GOVERNMENT LICENSE RIGHTS

This invention was made with government support under Cooperative Agreement No. EEC-1647722 awarded by the National Science Foundation. The government has certain rights in the invention.

BACKGROUND OF THE INVENTION

Field of the Invention

Embodiments provided herein relate to systems and processes for converting natural gas liquids to value-added products, including their corresponding olefin derivatives and/or liquid hydrocarbons. More particularly, such embodiments relate to systems and processes for processing natural gas liquid components from shale gas to provide one or more olefins and/or oligomers therefrom.

Description of the Related Art

Shale gas has become an increasingly important source of natural gas in the United States and it will become even more important in the future. The U.S. government's Energy Information Administration estimates that in 2017 about 62% of the total U.S. dry natural gas production comes from shale gas and by 2050, nearly 90% of the United States' natural gas production will come from shale resources. Shale gases contain substantial concentrations of natural gas liquids (NGLs), which are typically separated from methane gas at a natural gas processing plant. NGLs typically consist of $C_2H_6$, $C_3H_8$, $C_4H_{10}$ and $C_5H_{12}$.

Upgrading natural gas liquids (NGLs) to heavier liquid hydrocarbons is an attractive strategy to efficiently utilize shale gas resources. NGLs from remote shale gas formations, such as the Marcellus and Bakken fields, however, are usually flared at the wellhead or the gas processing plant since the cost of pipelines to transport the natural gas liquids to a downstream processing plant can be capital intensive. Upgrading natural gas liquids to heavier liquid hydrocarbons becomes attractive since it reduces the transportation cost and leads to more efficient utilization of NGLs.

Table 1 below provides a typical shale gas composition from wells at Barnett, Eagle Ford and Bakken fields. It is worth noting that methane ($CH_4$) is the predominant component of a shale gas stream (i.e. greater than 50 mol %). The combined mole fraction of all NGL components, $C_2$, $C_3$, $C_4$ and $C_{5+}$ alkanes, in a typical shale gas, generally varies from 5% to 40%. A few commercialized technologies are available for upgrading NGLs to liquid hydrocarbons, such as the UOP Cyclar™ process, Synfuels International ETG (Ethane to Gasoline), and Greyrock Direct Fuel Production™. In these processes, the separation between $CH_4$ and NGLs takes place prior to any NGL upgrading, as shown in FIG. 1.

FIG. 1 depicts a block flow diagram illustrating a conventional processing procedure for natural gas liquids where methane (CH4) is first removed from a sweet and dry shale gas and the remaining NGLs are sent for further processing to provide liquid hydrocarbon products. As shown in FIG. 1, sweet and dry shale gas stream 10 coming from the front-end gas treatment process is sent to a $CH_4/C_{2+}$ separation unit 110 in which the shale gas is separated into a methane ($CH_4$) rich stream 12 and an NGLs rich stream 11. The methane rich stream 12 is sent to a pipeline(s). The NGL rich stream 11 is sent to one or more processing units 120 for further separation and processing. The separation unit 110 for separating $CH_4$ from NGLs typically uses cryogenic distillation.

TABLE 1

Shale Gas Compositions (in mol %) from Wells at Barnett, Eagle Ford and Bakken fields.

|  | Barnett | Eagle Ford | Bakken |
|---|---|---|---|
| $CH_4$ | 85 | 74 | 58 |
| $C_2H_6$ | 6 | 14 | 20 |
| $C_3H_8$ | 2 | 5 | 11 |
| $C_4H_{10}$ | 2 | 3 | 4 |
| $C_{5+}$ | 0 | 2 | 1 |
| $N_2$ | 2 | 0 | 4 |
| $H_2O$ | 0.26 | 0.28 | 0.29 |
| $CO_2$ | 2 | 1 | 1 |
| $H_2S$ (mg/scf) | 335 | 307 | 115 |

FIG. 2 depicts a block flow diagram illustrating another system for producing liquid hydrocarbons (stream 23) wherein at least a portion of the processing steps 220, 230 towards natural gas liquids takes place prior to the $CH_4/C_{2+}$ separation unit 210. As shown, a natural gas stream 20 from a front-end gas treatment process is first processed in unit 230 to produce an effluent stream 24 that contains methane, hydrogen, and one or more other alkanes and alkenes. Stream 24 enters a separator 210 where methane via stream 22 is separated from a primarily heavier liquid stream 21 that is further processed in unit 220 to produce a liquid hydrocarbon product stream 23.

FIG. 3 depicts a block flow diagram illustrating another system for producing liquid hydrocarbon. In this system, a shale gas stream 30, which is usually obtained from a front-end natural gas treatment plant, is directly sent to a NGLs upgrading process that utilizes two upgrading processing steps: dehydrogenation 331 and oligomerization 332. In the dehydrogenation reactor 331, some of the NGLs are converted to their olefin derivatives. The olefins in stream 301 are then coupled into longer chain hydrocarbons in the oligomerization reactor 332. The separation between $CH_4$ and NGLs takes place after these two upgrading steps. Stream 34 coming out of the oligomerization reactor 332 is separated through a two-flash-drum system 312 and 313 into 3 streams: a liquid hydrocarbon stream 33, a $CH_4$-containing stream 32 contains predominantly $CH_4$ and $H_2$, with a small portion of $C_{2+}$, and a recycle stream 303 which contains predominantly $C_2$ to $C_5$ NGLs and their olefin derivatives. Stream 32 is further separated into a $CH_4$-rich stream 39 and a hydrogen ($H_2$) rich stream 38. In this case, the separation between $CH_4$ and $C_{2+}$ is through a flash drum 312. This separation is usually incomplete, which means stream 32 contains a significant amount of $C_{2+}$, which is lost and wasted since it is not converted to liquid hydrocarbons.

There is a need, therefore, for new and more efficient processes for producing liquid hydrocarbons from natural gas feeds.

SUMMARY OF THE INVENTION

Systems and processes for more efficiently upgrading natural gas liquids are provided. In at least one specific embodiment, the process for upgrading natural gas liquids can include providing a natural gas comprising methane and one or more natural gas liquids; converting at least a portion of the natural gas liquids to one or more liquid hydrocarbons; separating the methane from the one or more liquid hydrocarbons using a liquid absorbent to provide a first separated stream comprising the methane from the converted stream and a second separated stream comprising the one or more liquid hydrocarbons from the converted stream; and recycling at least a portion of the one or more liquid hydrocarbons as the liquid absorbent.

In at least one specific embodiment, the process for upgrading natural gas liquids can include providing a natural gas comprising methane and one or more $C_{2+}$ hydrocarbons; dehydrogenating at least a portion of the one or more $C_{2+}$ hydrocarbons into one or more $C_{2+}$ olefinic hydrocarbons to provide a first converted stream comprising methane and the one or more $C_{2+}$ olefinic hydrocarbons; oligomerizing the first converted stream to provide a second converted stream comprising methane and one or more C4 to C26 oligomers; separating the methane from the second converted stream using a liquid absorbent to provide a first separated stream comprising the methane from the second converted stream and a second separated stream comprising the one or more C4 to C26 oligomers from the second converted stream; and recycling at least a portion of the one or more C4 to C26 oligomers as the liquid absorbent.

In at least one other specific embodiment, the process for upgrading natural gas liquids can include providing a sweet and dry shale gas comprising at least 50 mol % methane and 5 mol % to 40 mol % one or more C2+ paraffins; dehydrogenating at least a portion of the one or more C2+ paraffins into one or more C2+ olefins to provide a first converted stream comprising methane and the one or more C2+ olefins; oligomerizing the first converted stream to provide a second converted stream comprising methane and one or more C4 to C26 oligomers; absorbing the methane from the second converted stream using a liquid absorbent to provide a first separated stream comprising the methane from the second converted stream and a second separated stream comprising the one or more C4 to C26 oligomers from the second converted stream; separating hydrogen from the methane in the first separated stream; separating gas from the one or more C4 to C26 oligomers in the second separated stream to provide an oligomer product comprising the one or more C4 to C26 oligomers; and recycling at least a portion of the oligomer product as the liquid absorbent.

BRIEF DESCRIPTION OF THE DRAWINGS

So that the manner in which the above recited features of the present invention can be understood in detail, a more particular description of the invention, briefly summarized above, can be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

The accompanying drawings are incorporated into and form a part of the specification to illustrate aspects and examples of the present disclosure. These figures together with the description serve to explain the general principles of the disclosure. The figures are only for the purpose of illustrating examples of how the various aspects of the disclosure can be made and used and are not to be construed as limiting the disclosure to only the illustrated and described examples.

FIG. 1 depicts a block flow diagram illustrating a conventional processing procedure for natural gas liquids where methane (CH4) via stream 12 is first removed from the sweet and dry shale gas (stream 10) and the remaining NGLs (stream 11) are sent for further processing in unit 120 to provide liquid hydrocarbon products (stream 13).

FIG. 2 depicts a block flow diagram illustrating another system for producing liquid hydrocarbons (stream 23) wherein at least a portion of the processing steps 220, 230 towards natural gas liquids takes place prior to the $CH_4/C_{2+}$ separation unit 210.

DETAILED DESCRIPTION

Figure 3:
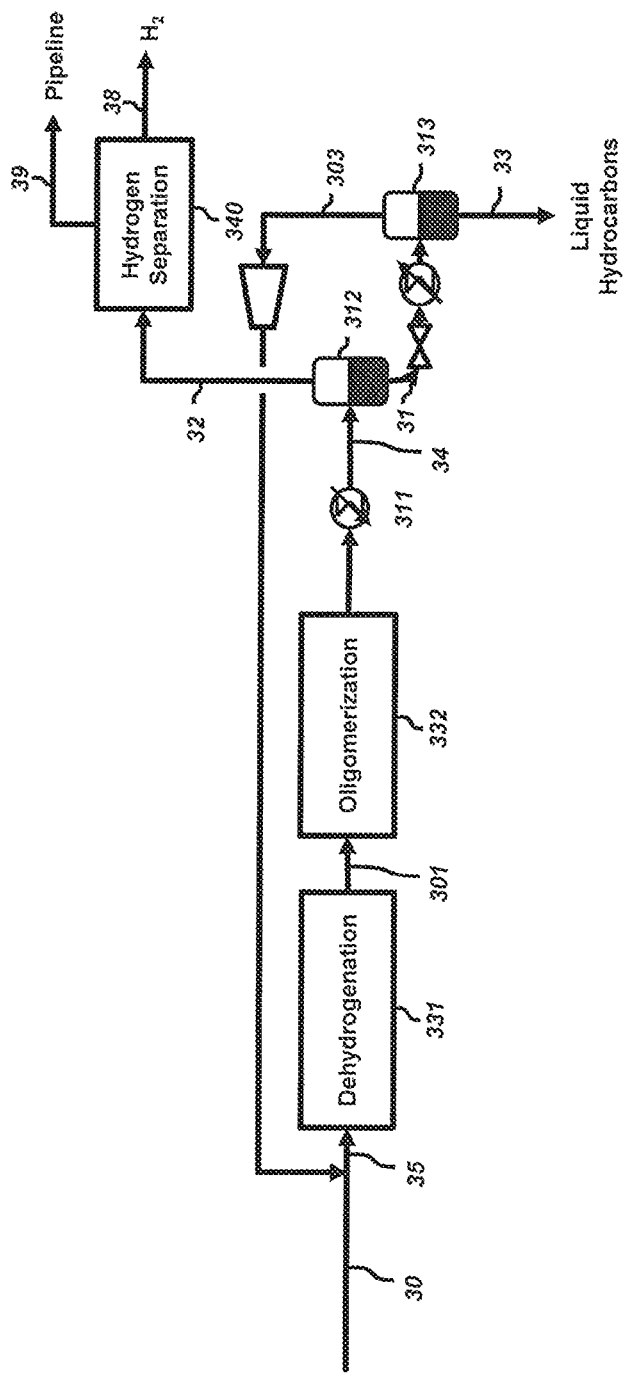
FIG. 3 depicts a block flow diagram illustrating another system for producing liquid hydrocarbon wherein a shale gas stream 30 passes through a dehydrogenation reactor 331 followed by an oligomerization reactor 332, the liquid hydrocarbons 33 are recovered as the product via a two-stage flash separation 312, 313, the $CH_4$-containing stream 39 is partially delivered to the pipeline after $H_2$ is separated 340 and the NGL stream 303 is recycled to the dehydrogenation unit 331.

A detailed description will now be provided. It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure can repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. The exemplary embodiments presented below also can be combined in any combination of ways, i.e., any element from one exemplary embodiment can be used in any other exemplary embodiment, without departing from the scope of the disclosure.

Additionally, certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function. Furthermore, in the following discussion and in the claims, the terms "including" and "comprising" are used in an open-ended fashion, and thus should be interpreted to mean "including, but not limited to."

The indefinite articles "a" and "an" refer to both singular forms (i.e., "one") and plural referents (i.e., one or more) unless the context clearly dictates otherwise.

The term "absorption" refers to the diffusion of gas and/or liquid particles into other liquid or solid materials. In the embodiments provided herein, any absorption system and process can be used. The absorber can be vertical or horizontal, and can be any type of vessel, column, or tower. The absorbent can flow co-current with the feed stream or counter current. In the embodiments that follow, a vertical absorber using counter-current flow is preferred, but not required.

The terms "absorber" and "absorption tower" both refer to a gas-liquid contactor, which can have trays or packing to enhance mass exchange surface area.

The term "acid gases" refers to carbon dioxide ($CO_2$) and hydrogen sulfide ($H_2S$) contained in raw shale gas.

The term "alkane" refers to saturated molecules containing hydrogen and carbon atoms only, in which all the carbon-carbon bonds are single bonds and are saturated with hydrogen. The term alkane encompasses linear, branched, and saturated cyclic alkanes.

The terms "alkene" and "olefin" are used interchangeably, and both refer to any unsaturated hydrocarbon molecule containing one or more pairs of carbon atoms linked by a double bond. Such unsaturated hydrocarbons include cyclic or aliphatic olefins, and include mono-olefins, di-olefins, tri-olefins, etc.

The term "CH4 containing stream" refers to a stream containing more than 50 mol % CH4.

The term "CH4 rich stream" refers to a stream containing more than 90 mol % methane (CH4).

The term "Cn" hydrocarbon wherein n is a positive integer, e.g., 1, 2, 3, 4, or 5 or more, means a hydrocarbon molecule having n number of carbon atom(s) per molecule. The term "Cn+" hydrocarbon wherein n is a positive integer, e.g., 1, 2, 3, 4, or 5 or more, means a mixture of hydrocarbon molecules containing two or more Cn hydrocarbons.

The phrase "consisting essentially of" means that the described/claimed composition does not include any other components that will materially alter its properties by any more than 5% of that property, and in any case, does not include any other component to a level greater than 3 wt %.

The term "hydrocarbon" refers to an organic compound that contains only hydrogen and carbon atoms.

The term "hydrocarbon stream" refers to any stream of hydrocarbons that is derived directly from a zone or formation within the earth. Illustrative hydrocarbon streams can be or can include a raw shale gas stream or raw natural gas stream or other raw hydrocarbon gaseous stream that is obtained directly (i.e. without processing to remove water and/or acid gas) from a reservoir, wellhead, or pipeline. Illustrative hydrocarbon streams can also be or can also include a natural gas stream that is obtained by passing raw natural gas pipelined from a reservoir or wellhead through one or more acid gas removal and dehydration units (i.e. after processing to remove water and/or acid gas). Suitable hydrocarbon streams can also originate from a refinery, such as from a FCC, coker, steam cracker, and pyrolysis gasoline (pygas). Suitable hydrocarbon streams can also be or can include shale gas, syngas and/or coal gas. For simplicity and ease of description the detailed description provided herein makes specific references to "shale gas" or "natural gas" or "sweet and dry shale gas"; however, those same embodiments equally apply to any hydrocarbon containing at least 50 mol % methane and at least 5 mol % NGL, regardless of how or where the hydrocarbon is obtained.

The term "H2 rich stream" refers to a stream containing more than 90 mol % hydrogen (H2).

The term "liquid hydrocarbon" refers to a hydrocarbon that is liquid at room temperature and ambient pressure.

The term "NGL alkene derivative" refers to any one or more C2+ alkenes derived from the dehydrogenation of NGL. Illustrative NGL alkene derivatives can be or can include one or more olefins having from about 2 to about 12 carbon atoms or more. Illustrative NGL alkene derivatives can also be or can also include one or more linear alpha olefins, such as ethene, propene, butenes, pentenes and/or hexenes.

The term "natural gas liquid" or "NGL" refers to any C2+ alkanes originally derived from a natural gas or shale gas stream, and primarily includes C2H6, C3H8, C4H10 and C5H12.

The terms "olefin derivative" and "alkene derivative" used interchangeably and refer to any unsaturated hydrocarbon that has the same carbon arrangement as another saturated hydrocarbon. The only difference between a saturated hydrocarbon and its olefin derivative or alkene derivative is the double bond.

The term "oligomer" refers to dimers, trimers, tetramers, and other molecular complexes having less than 26 repeating units. Oligomers provided herein are typically gases or liquids at ambient temperature, and can include low melting solids, including waxes, at ambient temperature. In some embodiments, the oligomers provided herein can have an atomic weight or molecular weight of less than 10,000 AMU (Da), such as about 5,000 or less, 1,000 or less, 500 or less, 400 or less, 300 or less, or 200 or less. The molecular weight of the oligomer, for example, can range from a low of about 50, 250 or 350 to a high of about 500, 3,000, 7,000, or 9,000 AMU (Da).

The term "oligomerization" refers to the formation of an oligomer from molecules of lower relative molecular mass. Any suitable oligomerization system and process can be used. The process can be carried out, for example, in a continuous stirred tank reactor, batch reactor, plug flow reactor, or bubble column reactor. One or more reactors operated in series or parallel can be used. The process can be operated at partial conversion to control the molecular weight of the product and unconverted olefins can be recycled for higher yields. Further, once the catalyst is deactivated with high molecular weight carbon, or coke, it can be regenerated using known techniques in the art, including for example, by combustion in air at a temperature of about 400° C. or higher.

The term "or" is intended to encompass both exclusive and inclusive cases, i.e., "A or B" is intended to be synonymous with "at least one of A and B," unless otherwise expressly specified herein.

The term "raw shale gas" refers to shale gas that is pipelined from reservoirs or wellheads prior to any further processing.

The term "shale gas" refers to natural gas that is produced from a shale or other tight formation, is a gaseous phase mixture containing natural gas liquids, acid gases, water, nitrogen (N2), and possibly trace amounts of contaminants A suitable shale gas (or natural gas) contains at least 50 mol % $CH_4$ and up to 40 mol % of $C_2H_6$, $C_3H_8$, $C_4H_{10}$, and/or $C_{5+}$ hydrocarbons. For example, a suitable shale gas (or natural gas) contains about 60 mol % to about 95 mol % $CH_4$ and about 5 mol % to about 40 mol % of $C_2H_6$, $C_3H_8$, $C_4H_{10}$, and/or $C_{5+}$ hydrocarbons (or collectively referred to as "$C_{2+}$ hydrocarbons" or "$C_{2+}$ alkanes"). Among the $C_{2+}$ hydrocarbons, $C_2H_6$ is generally the highest concentration followed by $C_3H_8$ then $C_4H_{10}$. Nitrogen gas ($N_2$) can also be present in the shale gas.

The term "sweet and dry shale gas" refers to shale gas obtained after acid gases and water have been removed from the raw shale gas. Insignificant amounts of other components in the sweet shale gas can be removed together with water and thus, a sweet and dry shale gas has almost all the components contained in raw shale gas except acid gases and water. Since acid gases and water can be in relatively small concentration, the composition of the sweet and dry shale gas is similar, or substantially the same, as that of the raw shale gas.

The term "sweet shale gas" refers to shale gas obtained after the acid gases have been removed from the raw shale gas. Insignificant amounts of other components in the raw shale gas can be removed together with acid gases and thus, a sweet shale gas has almost all the components contained in raw shale gas except acid gases.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

The following detailed description illustrates embodiments of the present disclosure. These embodiments are described in sufficient detail to enable a person of ordinary skill in the art to practice these embodiments. It should be understood, however, that the embodiments and examples described herein are given by way of illustration only, and not by way of limitation, the embodiments are chosen and described so that others skilled in the art may appreciate and understand the principles and practices of the present teachings. Various substitutions, modifications, additions, and rearrangements can be made that remain potential applications of the disclosed processes. Therefore, the description that follows is not to be taken as limiting on the scope of the appended claims. In particular, an element associated with a particular embodiment should not be limited to association with that particular embodiment but should be assumed to be capable of association with any embodiment discussed herein.

Figure 4:
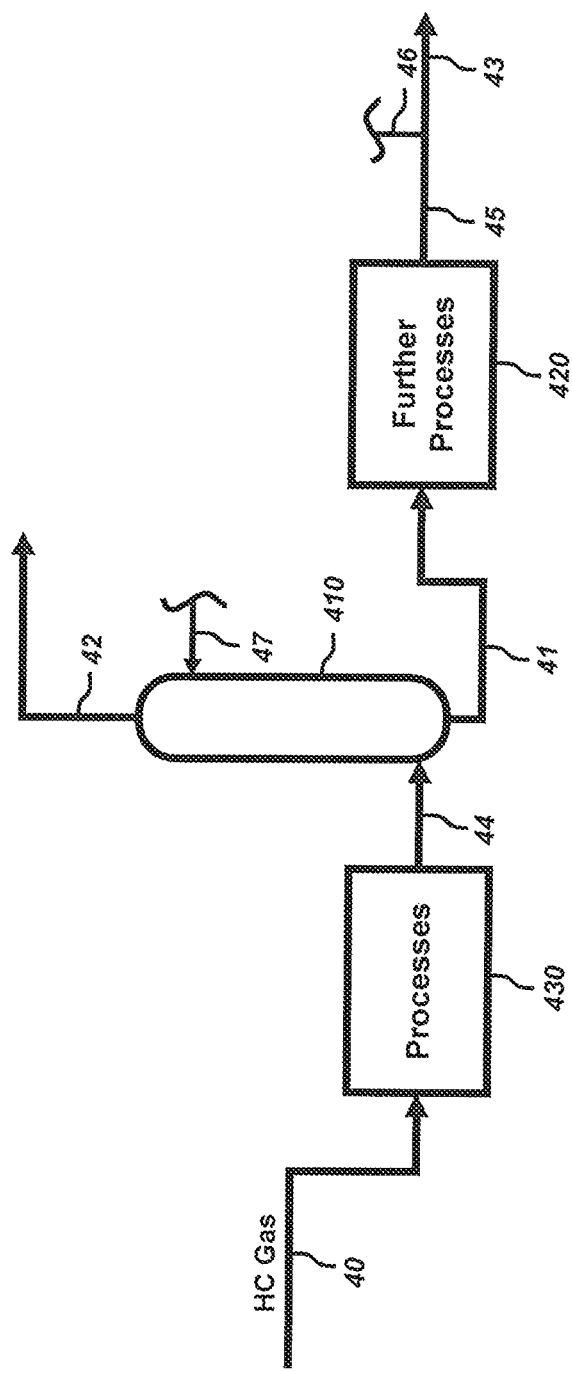
FIG. 4 depicts a flow diagram of an illustrative NGL upgrading system, according to or more embodiments provided herein, wherein at least a portion of the liquid hydrocarbon product of the NGLs upgrading process is used as the absorbent for the absorption process to recover $C_{2+}$ from a gaseous stream.

FIG. 4 depicts a flow diagram of an illustrative NGL upgrading system, according to or more embodiments provided herein. As depicted, at least a portion of the liquid hydrocarbon product 43, 45 of the NGLs upgrading process is used as an absorbent 47 for an absorption system 410 for recovering $C_{2+}$ (stream 42) from a hydrocarbon gas stream 40. The gas stream 40 can contain any one or more hydrocarbon gas, natural gas, shale gas, or any sweet and dry gas thereof. The gas stream 40 first passes through one or multiple upgrading steps in processing unit 430. At least a portion of the NGLs can be converted to one or more other compounds, such as one or more NGL alkene derivatives and/or other liquid hydrocarbons. After that, the stream 44 that contains $CH_4$ and $C_{2+}$ can flow to an absorption tower 410 in which $CH_4$ and $C_{2+}$ can be separated. A methane rich stream exits the top of the absorber 410 via stream 42 and a methane lean stream exits the bottom of the absorber 410 via stream 41. This methane lean stream/C2+ rich stream 41 from the bottom of the absorption tower 410 can be further processed in processing unit 420. An upgraded natural gas liquid stream 45 exits the processing unit 420. A portion of the upgraded liquid hydrocarbon product in stream 45 can be fed via streams 46, 47 to the absorption tower 410 as the absorbent. Anywhere from 1% to 99% of the upgraded liquid hydrocarbon product in stream 45 can be fed via streams 46, 47 to the absorption tower 410 as the absorbent. In some cases, the amount of the upgraded liquid hydrocarbon product in stream 45 that is recycled to the absorption tower 410 can range from a low of about 1%, about 3%, about 5%, about 10%, or about 15% to a high of about 15%, about 50%, about 75%, about 95%, or about 95%. The processing units 420, 430 can be a single processing step, multiple processing steps, or one of these units may not exist. For example, if the upgrading process is a dehydrogenation reaction which converts at least a portion of NGLs to alkene derivatives, followed by an oligomerization reaction which converts a portion of the alkenes to heavier alkenes ($C_{5+}$), then the processing unit 430 can be a dehydrogenation reactor and the processing unit 420 can be a series of oligomerization reactors and separators. Alternatively, the processing unit 430 can be a dehydrogenation reactor and an oligomerization reactor and the processing unit 420 can be one or more separation towers or fractionators.

Figure 5:
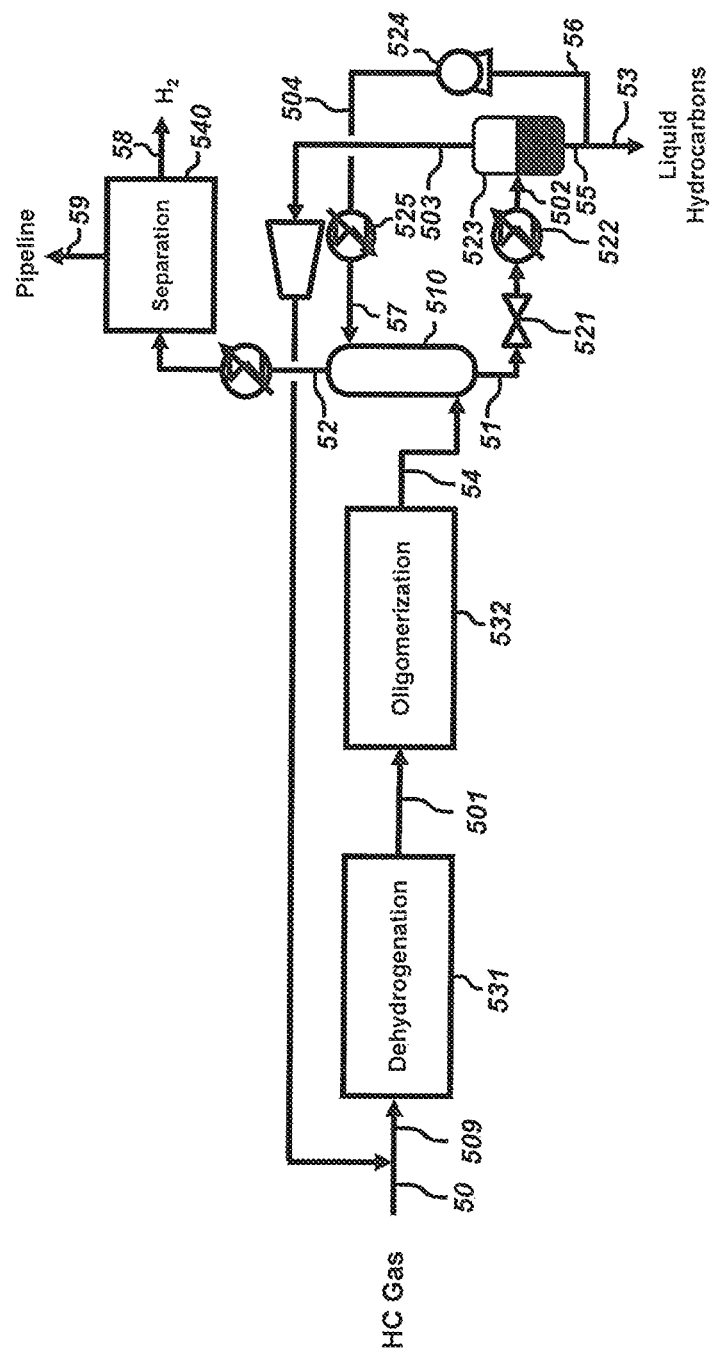
FIG. 5 depicts a flow diagram of another illustrative NGL upgrading system, according to or more embodiments provided herein, wherein a shale gas stream passes through a dehydrogenation reactor followed by an oligomerization reactor, the liquid hydrocarbons are recovered as the product via an absorption tower followed by a flash separation, the $CH_4$-containing gas stream from the absorption tower is delivered to the pipeline after $H_2$ is separated, the gas from the flash drum is recycled to the dehydrogenation reactor, and a portion of the liquid hydrocarbons is used as the absorbent of the absorption tower.

FIG. 5 depicts a flow diagram of another illustrative NGL upgrading system, according to or more embodiments provided herein. A hydrocarbon gas stream 50 can flow through a dehydrogenation reactor 531 followed by an oligomerization reactor 532. The gas stream 50 can contain any one or more hydrocarbon gas, natural gas, shale gas, or any sweet and dry gas thereof. Liquid hydrocarbons 53 can be recovered as the product via an absorption tower 510 followed by a flash separation in separator 523. The $CH_4$-containing gas stream 52 from the absorption tower 510 can be delivered to a pipeline 59 after H$_2$ in stream 458 has been separated via separator 540. Gas from the flash drum 523 can be recycled to the dehydrogenation reactor via stream 503, and a portion of the liquid hydrocarbons via stream 504 can be used as the absorbent in the absorption tower 510. As shown in FIG. 5, the upgrading process of NGLs can be achieved by a dehydrogenation unit 531 followed by an oligomerization unit 532. In this embodiment, the dry and sweet shale gas stream 50 can flow to the dehydrogenation unit 531 without any separation steps. This dehydrogenation unit 531 can be operated at any pressure between 1 bar and 30 bar, and at any temperature between 550° C. and 990° C. The operating temperature and pressure can change to meet any design specifications.

In the dehydrogenation unit/reactor 531, a portion of NGLs in stream 509 can be converted to one or more alkene derivatives and H$_2$. Since the thermodynamic equilibrium limits the conversion of this reaction, the outlet stream 501 from this reactor 531 can be a mixture of H$_2$, CH$_4$, NGLs, and NGL alkene derivatives. This mixture stream 501 can then flow to the oligomerization reactor 532 in which a portion of the NGL alkene derivatives can be oligomerized into one or more C$_{5+}$ alkenes.

The oligomerization unit/reactor 532 generally operates at a higher pressure (up to 30 bar) and a relatively lower temperature (25° C. to 450° C.). The typical operating pressure ranges from about 5 bar to about 30 bar and the operating temperature typically ranges from about 100° C. to about 300° C. The outlet stream 54 from the oligomerization unit 532 can be a mixture of H$_2$, CH$_4$, NGLs, NGL alkene derivatives, and one or more C$_{5+}$ alkenes.

The outlet mixture 54 enters the absorption tower 510 in which almost all the NGLs, NGL alkene derivatives, and one or more C$_{5+}$ alkenes are absorbed into the liquid phase. This absorption tower operates at −20° C. in order to remove almost all the C$_{2+}$ from the gas phase. The CH$_4$-gas stream 52 from the absorption tower 510 can include CH$_4$ and H$_2$. The CH$_4$-gas stream 52 can be separated into a CH$_4$-rich stream 59 and a H$_2$-rich stream 58 in the separation unit 540. This separation unit could be any separation techniques such as distillation, membrane, membrane cascade, etc. Besides being sent to pipelines, the CH$_4$-rich stream 59 could also go through further upgrading processes or directly burned to supply heat to the entire flowsheet. The CH$_4$-rich stream 59 could be used in various situations and should not be restrained to the scenarios mentioned above. The liquid stream from the absorption tower can pass through a J-T valve 521 and then a heat exchanger 522 where the stream 502 can adjusted to near ambient pressure and temperature. After that this stream is separated into a liquid stream 55 and a vapor stream 503 in the flash drum 523. The liquid stream 55 can include liquid hydrocarbons and the vapor stream 503 can include NGLs and their alkene derivatives. A portion of the liquid hydrocarbon stream 55 in line 56 is pumped through a pump 524 and is cooled to around −20° C. in unit 525 and fed to the absorption tower 510 as an absorbent in line 57. The vapor stream 503 is compressed and recycled back to the dehydrogenation reactor 531.

Anywhere from 1% to 99% of the liquid hydrocarbon stream 55 can be fed to the absorption tower 510 via stream 57 as the absorbent. In some cases, the amount of the liquid hydrocarbon that is recycled to the absorption tower 510 can range from a low of about 1%, about 3%, about 5%, about 10%, or about 15% to a high of about 15%, about 50%, about 75%, about 95%, or about 95%.

It is worth noting that in FIG. 5, there might be one or more heat exchangers or one or more compressors/expanders prior to the two reactors 531, 532 to adjust the temperature and pressure of the inlet streams 509 and 501 to the same temperature and pressure as the reactors 531, 532. Particularly, if the dehydrogenation reactor 531 is operated at the same pressure as the oligomerization reactor 532, the compressor between these two reactors is no longer needed.

Figure 6:
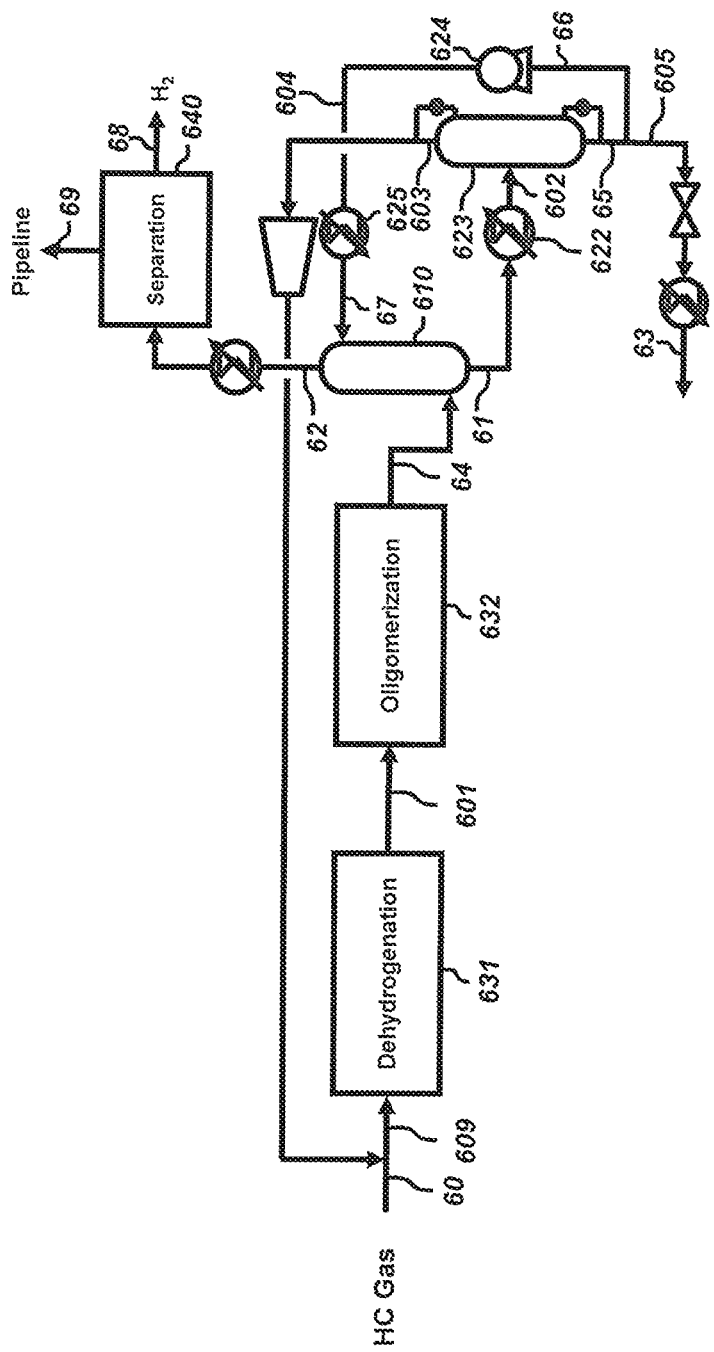
FIG. 6 depicts a flow diagram of another illustrative NGL upgrading system, according to or more embodiments provided herein, wherein a shale gas stream passes through a dehydrogenation reactor followed by an oligomerization reactor, the liquid hydrocarbons are recovered as the product via an absorption tower followed by a distillation column, the $CH_4$-containing gas stream from the absorption tower is delivered to the pipeline after $H_2$ is separated, the gas from the distillation column is recycled to the dehydrogenation reactor, and a portion of the liquid hydrocarbons is used as the absorbent of the absorption tower.

FIGS. 6-11 depict alternative embodiments to the two step (dehydrogenation followed by oligomerization) upgrading process described above with reference to FIG. 5. Referring to FIG. 6, a hydrocarbon gas 60 can be fed to a dehydrogenation reactor 631 and then flows through an oligomerization reactor 632. The gas stream 60 can contain any one or more hydrocarbon gas, natural gas, shale gas, or any sweet and dry gas thereof. The stream 64 exiting the oligomerization reactor can be fed to an absorption tower 610 and separated into two streams: (1) the CH$_4$-containing gas stream 62 that is further separated into a CH$_4$-rich stream 69 and a H$_2$-rich stream 68, and (2) a liquid stream 61 containing C$_{2+}$ liquid hydrocarbons. A distillation column 623 can used instead of the flash drum 523 (FIG. 5) to separate any gaseous components from the liquid stream 61. The filled circle at the bottom of the distillation column 623 represents a reboiler and the filled circle at the top of the distillation column 623 represents a condenser. The C$_{2+}$ hydrocarbons contained in liquid stream 61 can be pre-heated using a heat exchanger 622 prior to the distillation column 623. The pre-heated stream 602 can then be separated into a gas stream 603 and a liquid stream 65. The gas stream 603 includes unconverted NGLs and their alkene derivatives and can be recycled back to the dehydrogenation reactor 631. The liquid stream 65 contains mainly liquid hydrocarbons and a portion thereof can flow to the absorption tower 610 as the absorbent via stream 67.

Anywhere from 1% to 99% of the liquid stream 65 can be fed to the absorption tower 610 via stream 67 as the absorbent. In some cases, the amount of the liquid stream that is recycled to the absorption tower 510 can range from a low of about 1%, about 3%, about 5%, about 10%, or about 15% to a high of about 15%, about 50%, about 75%, about 95%, or about 95%.

The distillation column 623 can be operated at a similar pressure to that of the absorption column 523. The reboiler temperature of the column 623 can about 200° C. to about 300° C. The temperature of the feed stream 64 to the distillation column 623 could be higher (about −10° C.) than the temperature of stream 54 in FIG. 5, and still provide similar liquid hydrocarbon yields. This will reduce the cooling utilities required for this configuration. It should also be mentioned that although it is not shown in FIG. 6, the distillation unit 623 could be adjusted to a distillation sequence that separates stream 602 into multiple product streams, depending on the different outlet composition of the oligomerization reactor 632 and the specific products desired. If multiple products are produced, it is preferred that only the heaviest product stream is fed to the absorption tower 610 as the absorbent stream 67.

One benefit of the embodiments described with reference to FIG. 6 is that, the pressure of the recycle stream 603 is higher, which means only small compression work is needed when recycling stream 603 back to the dehydrogenation reactor 631. Meanwhile, it provides some flexibility to get various products by adjusting the reboiler temperature of the distillation tower 623 as well as changing the single distillation column to a distillation column sequence.

Figure 7:
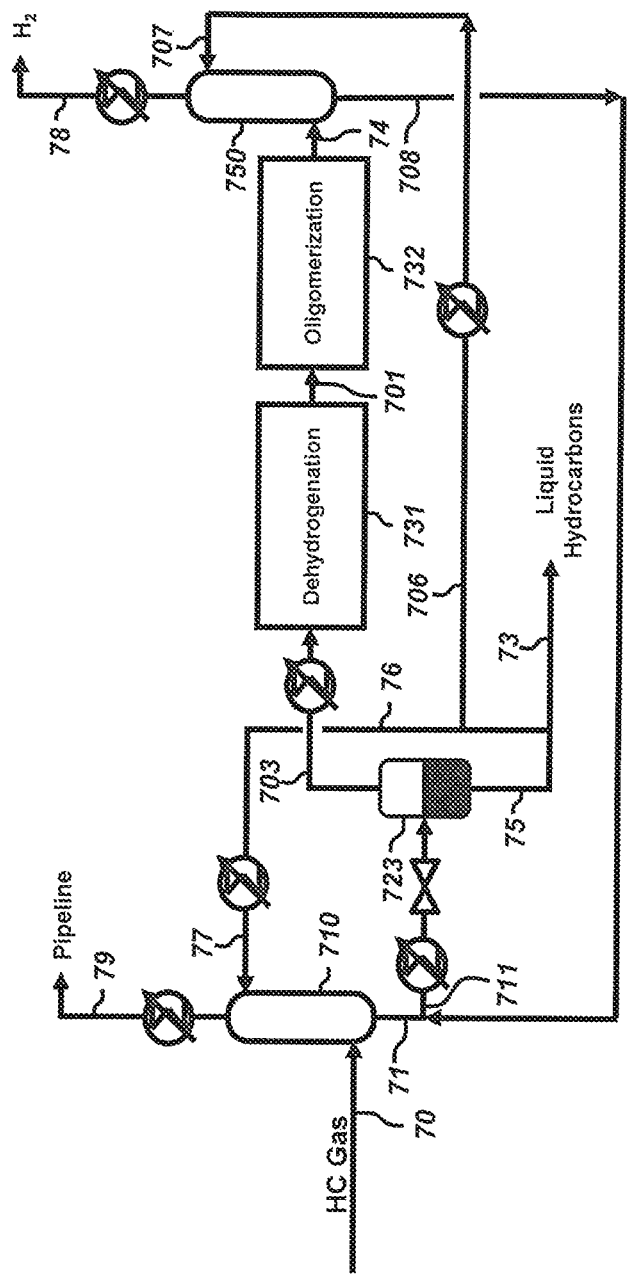
FIG. 7 depicts a flow diagram of another illustrative NGL upgrading system, according to or more embodiments provided herein, wherein a shale gas stream passes through an absorption tower followed by a flash drum, a $CH_4$-rich gas stream is recovered from the absorption tower and delivered to the pipeline, liquid hydrocarbons are recovered as a liquid product from the flash drum, the gas stream from the flash drum passes through a dehydrogenation reactor followed by an oligomerization reactor and a $H_2$-rich stream is recovered via another absorption tower, the liquid stream from the second absorption tower is recycled to the flash drum, and portions of the liquid hydrocarbons are used as absorbents for the two absorption towers. This embodiment shows an additional aspect of the invention where $C_{2+}$ hydrocarbons are separated from a $H_2$-rich stream.

FIG. 7 depicts a flow diagram of another illustrative NGL upgrading system, according to or more embodiments provided herein. This system utilize two or more absorption systems. Referring to FIG. 7, a hydrogen gas stream 70 can be fed to a first absorption tower 710 and separated into a $CH_4$-rich stream 79 and a $C_{2+}$ alkanes liquid stream 71. The gas stream 70 can contain any one or more hydrocarbon gas, natural gas, shale gas, or any sweet and dry gas thereof. The liquid stream 71 can be a mixture of NGLs and the absorbent (liquid hydrocarbons). This liquid stream can be further separated into a vapor stream 703 which contains mainly NGLs and a liquid stream 75 which contains mainly liquid hydrocarbons. A portion of the liquid hydrocarbons 75 can be fed to the absorption tower 710 as the absorbent via streams 76, 77. The gas stream 703 can be fed to a dehydrogenation reactor 731 and then an oligomerization reactor 732. After passing through these two reactors, stream 74 can be fed to a second absorption tower 750 where $H_2$ can separated from $C_{2+}$ hydrocarbons. The gas stream 78 mainly contains $H_2$ and the liquid stream 708 mainly contains $C_{2+}$ hydrocarbons. The second absorption tower 750 also uses a portion of the liquid hydrocarbon product 706 as the absorbent via stream 711. The liquid stream 708 containing $C_{2+}$ hydrocarbons can be mixed with liquid stream 71 and the combined stream can be heated and reduced in pressure, as necessary, such as through a Joule-Thompson (J-T) let-down valve, and fed to the separator 723. Stream 73 is the liquid hydrocarbon product stream.

Anywhere from 1% to 99% of the liquid hydrocarbons 75 can be fed to the absorption tower 710 via streams 76, 77 as the absorbent. In some cases, the amount of the liquid hydrocarbons that is recycled to the absorption tower 710 can range from a low of about 1%, about 3%, about 5%, about 10%, or about 15% to a high of about 15%, about 50%, about 75%, about 95%, or about 95%.

One benefit of the embodiments referred in FIG. 7, compared to the system of FIG. 5, is that very little $CH_4$ exists in either the dehydrogenation reactor 731 or the oligomerization reactor 732. Therefore, it avoids the separation between $CH_4$ and $H_2$.

Figure 8:
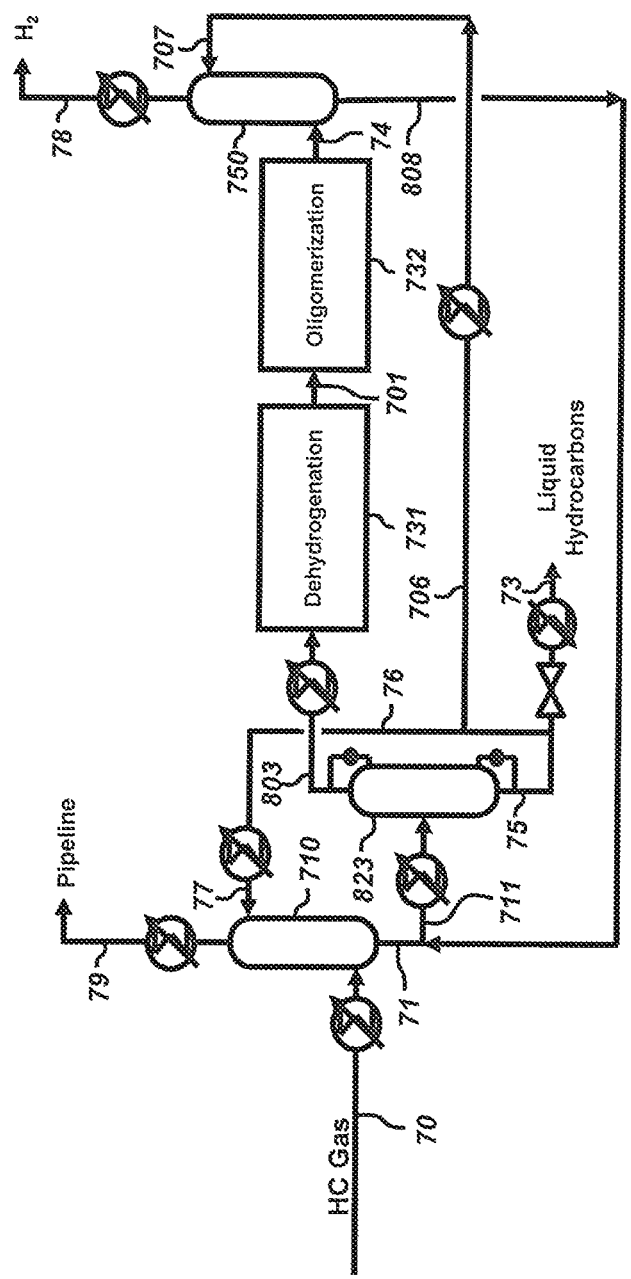
FIG. 8 depicts a flow diagram of another illustrative NGL upgrading system, according to or more embodiments provided herein, wherein a shale gas stream passes through an absorption tower followed by a distillation column, a $CH_4$-rich stream is recovered from the absorption tower and delivered to the pipeline, liquid hydrocarbons are recovered as a liquid product from the distillation column, the gas stream from the distillation column passes through a dehydrogenation reactor followed by an oligomerization reactor and a $H_2$-rich stream is recovered via another absorption tower, the liquid stream from the second absorption tower is recycled to the distillation column, and portions of the liquid hydrocarbons are used as absorbents for the two absorption towers.

FIG. 8 depicts a flow diagram of another illustrative NGL upgrading system, according to or more embodiments provided herein. This system differs from the system of FIG. 7 in that liquid stream 711 can be separated using a distillation column 823, instead of the separator 723. The filled circle at the bottom of the distillation column 823 represents a reboiler and the filled circle at the top of the distillation column 823 represents a condenser. The distillation column 823 provides additional flexibility to obtain various products by adjusting the reboiler temperature of the distillation tower 823 as well as changing the single distillation column to a series of distillation columns.

As depicted in FIGS. 7 and 8, the $CH_4$ and $C_{2+}$ can be separated in the front end of the process. The operating condition of the reactors, the choice of separation techniques and devices, and the related operating equipment for these two embodiments are similar to those in the embodiments referred in FIGS. 5 and 6. However, the orders of those processing units are different.

Figure 9:
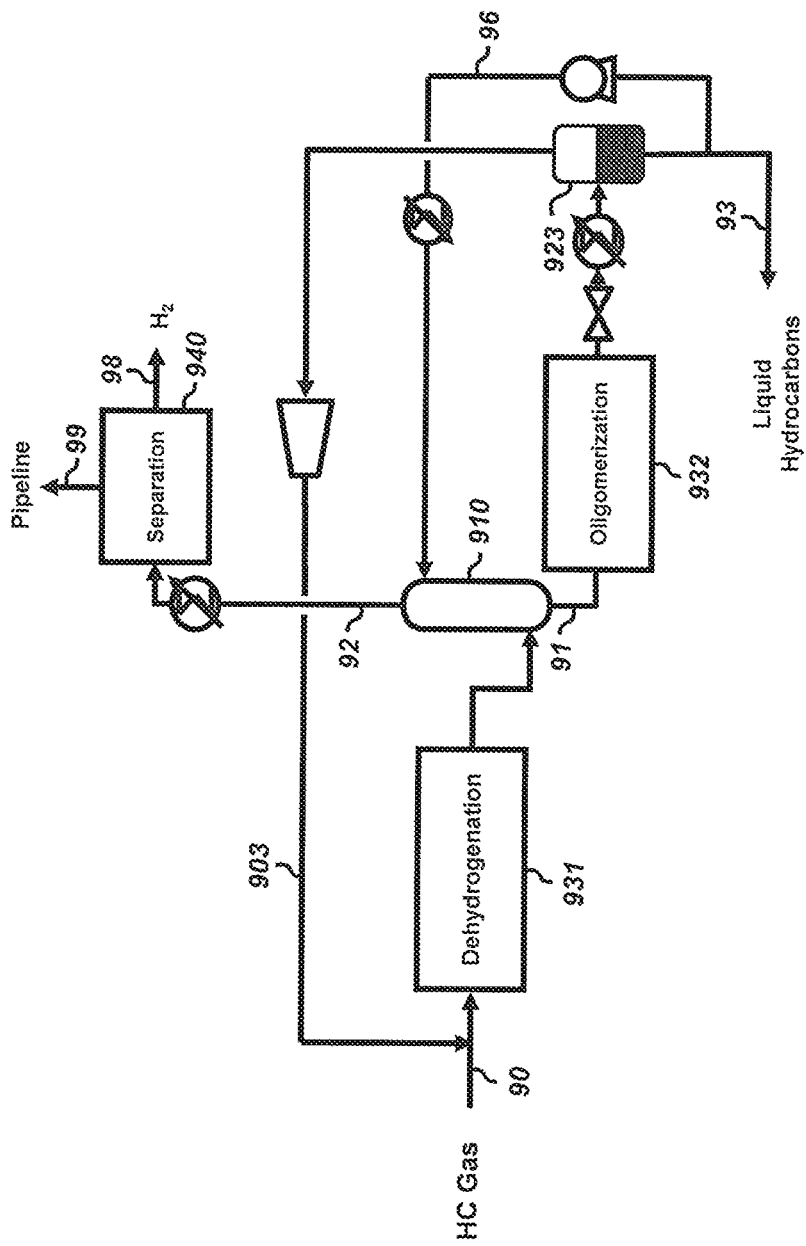
FIG. 9 depicts a flow diagram of another illustrative NGL upgrading system, according to or more embodiments provided herein, wherein a shale gas stream passes through a dehydrogenation reactor, a $CH_4$ containing stream is recovered via an absorption tower, a $CH_4$-rich stream is delivered to the pipeline after $H_2$ is recovered, the remaining stream from the absorption tower passes through an oligomerization reactor and liquid hydrocarbons are recovered via a flash drum, the gas stream from the flash drum is recycled back to the dehydrogenation reactor and a portion of the liquid hydrocarbons is used as the absorbent of the absorption tower.
Figure 10:
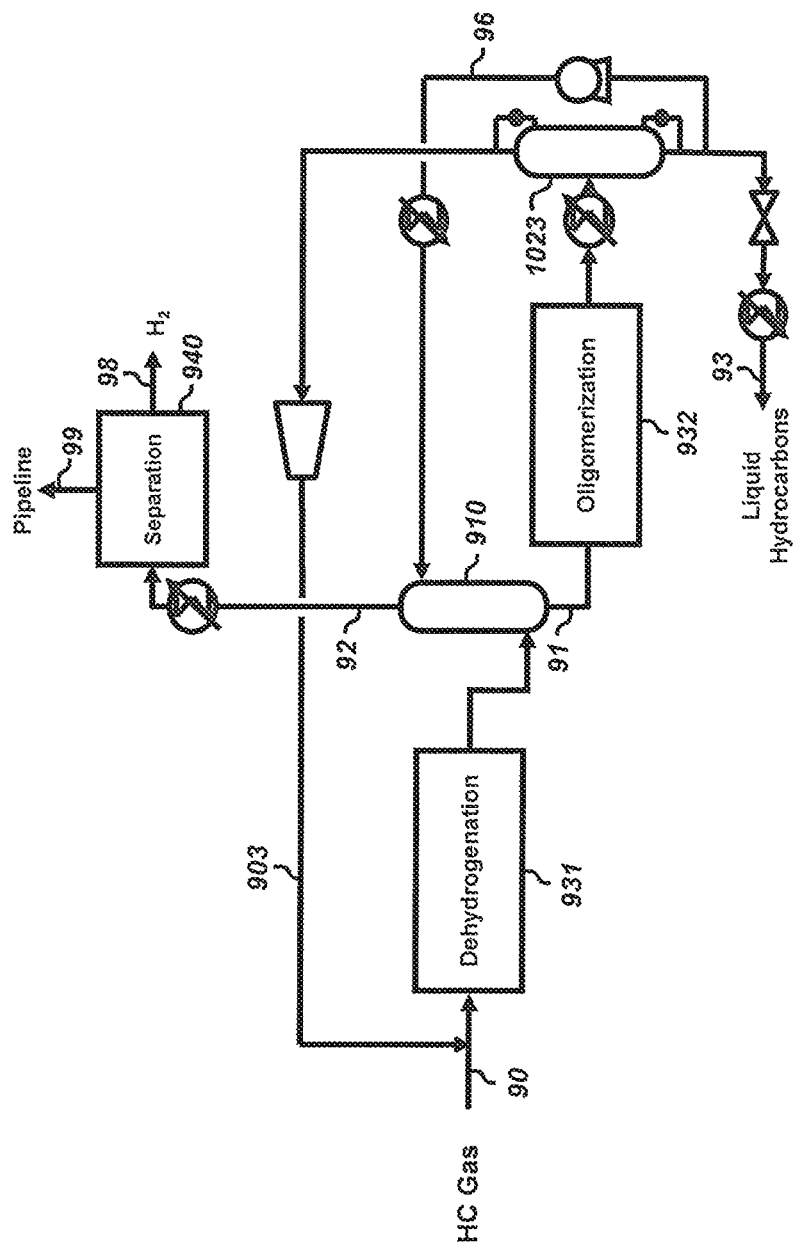
FIG. 10 depicts a flow diagram of another illustrative NGL upgrading system, according to or more embodiments provided herein, wherein a shale gas stream passes through a dehydrogenation reactor, a $CH_4$-containing stream is recovered via an absorption tower, a $CH_4$-rich stream is delivered to the pipeline after $H_2$ is recovered, the remaining stream from the absorption tower passes through an oligomerization reactor and is separated via a distillation column, the gas stream from the distillation column is recycled back to the dehydrogenation reactor and a portion of the liquid hydrocarbons is used as the absorbent of the absorption tower.

FIGS. 9 and 10 depict alternative embodiments where the separation of $CH_4$ and $C_{2+}$ can occur between the dehydrogenation reactions 931 and the oligomerization reactions 932. Referring first to FIG. 9, a hydrocarbon gas stream 90 can flow through a dehydrogenation reaction unit 931 followed by $CH_4$ and $C_{2+}$ separation using an absorption unit or tower 910. The gas stream 90 can contain any one or more hydrocarbon gas, natural gas, shale gas, or any sweet and dry gas thereof. The liquid hydrocarbons exiting the tower 910 via stream 91 then pass through the oligomerization reaction unit 932. The liquid hydrocarbons can be recovered using flash drum 923 via stream 93, and the gas stream 903 from the flash drum 923 can be recycled back to the dehydrogenation reaction unit 931. A portion of the liquid hydrocarbons 93 from the bottoms of the flash drum 923 can be used as the absorbent (via stream 96) for the absorption tower 910. The $CH_4$-containing gas stream 92 from the absorption tower 910 can be delivered to a pipeline 99 after $H_2$ in stream 98 has been separated via separator 940.

Alternatively, this liquid stream 91 can be further separated into a liquid hydrocarbon stream and a gaseous stream containing predominantly light alkenes $C_2$ through $C_4$, which can be fed to the oligomerization reactor 932. The separated liquid hydrocarbon stream can be mixed with the product stream 93 as part of the product.

Anywhere from 1% to 99% of the liquid hydrocarbons 93 can be fed to the absorption tower 910 via stream 96 as the absorbent. In some cases, the amount of the liquid stream that is recycled to the absorption tower 910 can range from a low of about 1%, about 3%, about 5%, about 10%, or about 15% to a high of about 15%, about 50%, about 75%, about 95%, or about 95%.

The embodiment in FIG. 10 differs from the embodiment in FIG. 9 only when separating the liquid stream 91 coming out of the absorption tower 910. As depicted in FIG. 10, a distillation column 1023 can be used in lieu of or in addition to the separator 923. The operating condition of the reactors 931, 932, the choice of separation techniques and devices, and the related operating equipment for these two embodiments depicted in FIGS. 9 and 10 are similar to those in the embodiments referred in FIG. 5 and FIG. 6.

FIGS. 11 through 16 depict alternative upgrading systems according to one or more other embodiments. In these embodiments, a three-step upgrading process containing dehydrogenation, oligomerization, and hydrogenation can be used. In the processes depicted by FIGS. 11 to 16, a hydrogenation unit can be used downstream of the oligomerization unit. For the embodiments depicted in FIGS. 11 through 14, the rest of the embodiments can be identical to the embodiments in FIGS. 5 through 8, respectively. For FIGS. 15 and 16, a portion of the $H_2$-rich stream can be fed to the hydrogenation unit. In the hydrogenation unit, a portion of the alkenes can react with $H_2$ to provided one or more liquid alkane hydrocarbon products. These products are typically more stable for transportation and storage. It is worth noting that, any other configuration that can be synthesized by rearranging the processing units of the embodiments mentioned in this invention is also included in this invention. A more detailed discussion of FIGS. 11 to 16 is provided below.

Figure 11:
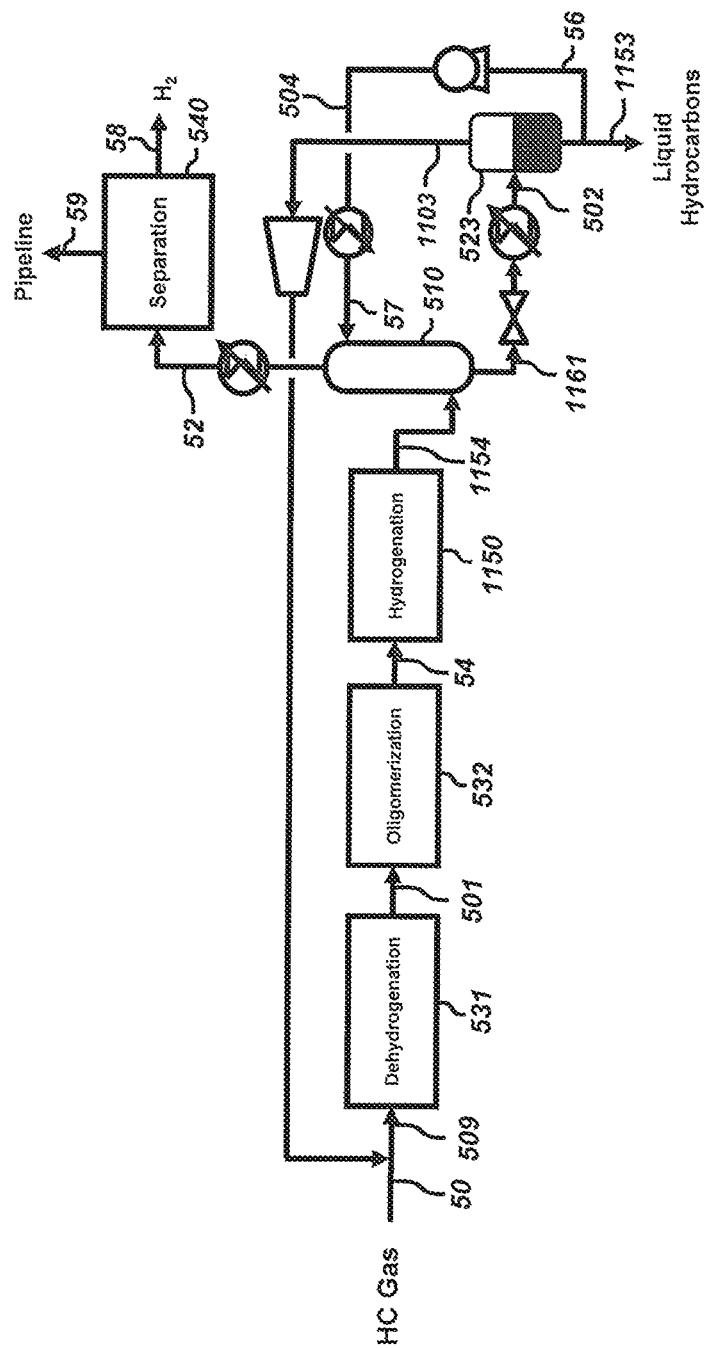
FIG. 11 depicts a flow diagram of another illustrative NGL upgrading system, according to or more embodiments provided herein, wherein a shale gas stream passes through a reactor sequence can include a dehydrogenation reactor, an oligomerization reactor, and a hydrogenation reactor, the liquid hydrocarbons are recovered as the product via an absorption tower followed by a flash separation, the $CH_4$-containing stream from the absorption tower is delivered to the pipeline after $H_2$ is separated, the gas stream from the flash drum is recycled to the dehydrogenation reactor, and a portion of the liquid hydrocarbons is used as the absorbent of the absorption tower.

Referring to FIG. 11 in more detail, a shale gas stream 50 passes through a reactor sequence that includes a dehydrogenation unit/reactor 531, an oligomerization unit/reactor 532, and a hydrogenation unit/reactor 1150. Downstream from the hydrogenation unit/reactor 1150, the liquid hydrocarbons via stream 1154 can flow to the absorption tower 510 followed by a flash separation in separator 523. The $CH_4$-containing stream 52 from the absorption tower 510 can be delivered to the pipeline 59 after $H_2$ is separated in separator 540 via stream 58. The gas stream 503 from the flash drum 523 can be recycled to the dehydrogenation reactor/unit 531. The liquid hydrocarbon products can be recovered from the bottoms of the separator 523. Any portion of the liquid hydrocarbons 1153 can be used as the absorbent via stream 56 to the absorption tower 510.

Figure 12:
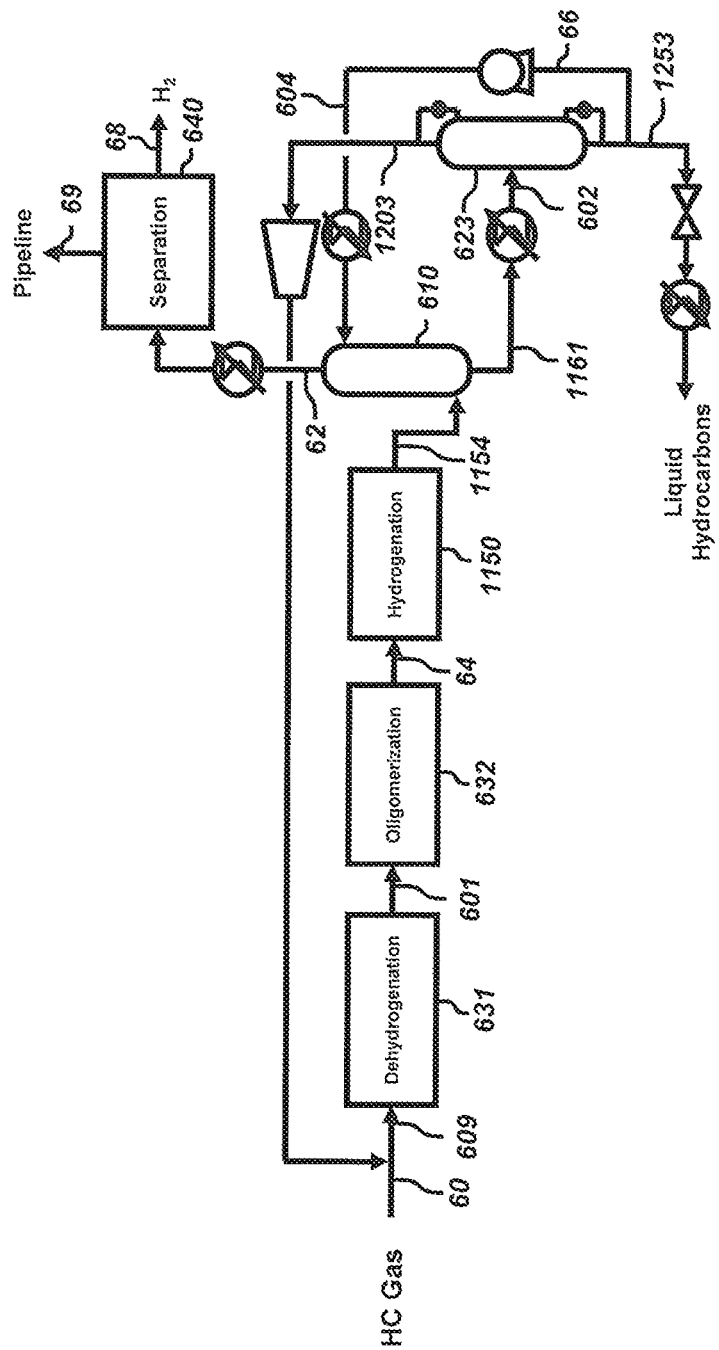
FIG. 12 depicts a flow diagram of another illustrative NGL upgrading system, according to or more embodiments provided herein, wherein a shale gas stream passes through a reactor sequence can include a dehydrogenation reactor, an oligomerization reactor, and a hydrogenation reactor, the liquid hydrocarbons are recovered as the product via an absorption tower followed by a distillation column, the $CH_4$-containing stream from the absorption tower is delivered to the pipeline after $H_2$ is separated, the gas stream from the distillation column is recycled to the dehydrogenation reactor, and a portion of the liquid hydrocarbons is used as the absorbent of the absorption tower.

With reference to the system described above in regard to FIG. 6, the system of FIG. 12 allows the liquid hydrocarbon products 1253 to be recovered via the absorption tower 610 followed by distillation column 623. The $CH_4$-containing stream 62 from the absorption tower 610 can be delivered to the pipeline 69 after $H_2$ is separated via stream 68 from the separator 640. The gas stream 603 from the distillation column 623 can be recycled to the dehydrogenation reactor 631, and a portion of the liquid hydrocarbons 1253 can be used as the absorbent (via stream 66) to the absorption tower 62.

Figure 13:
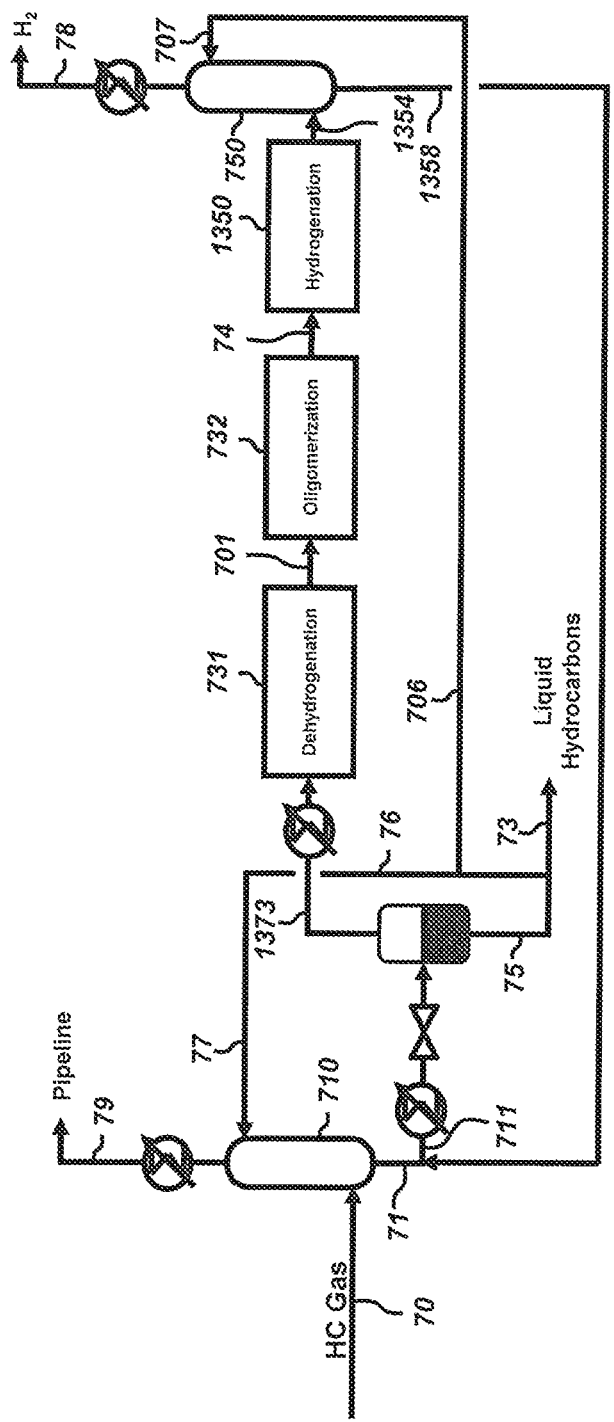
FIG. 13 depicts a flow diagram of another illustrative NGL upgrading system, according to or more embodiments provided herein, wherein a shale gas stream passes through an absorption tower followed by a flash drum, a $CH_4$-rich stream is recovered from the absorption tower and delivered to the pipeline, liquid hydrocarbons are recovered as a liquid product from the flash drum, the gas stream from the flash drum passes through a reactor sequence can include a dehydrogenation reactor, an oligomerization reactor, a hydrogenation reactor and a $H_2$-rich stream is recovered via another absorption tower, the liquid stream from the second absorption tower is recycled to the flash drum, and portions of the liquid hydrocarbons are used as absorbents for the two absorption towers. This embodiment shows an additional aspect of the invention where $C_{2+}$ hydrocarbons are separated from a stream that is enriched in $H_2$.

FIG. 13 depicts a flow diagram of another illustrative NGL upgrading system. In this embodiment, a shale gas stream passes through an absorption tower followed by a flash drum. A $CH_4$-rich stream can be recovered from the absorption tower and delivered to the pipeline. Liquid hydrocarbons can be recovered as a liquid product from the flash drum. The gas stream from the flash drum can flow through the reactor sequence of a dehydrogenation reactor, an oligomerization reactor, and a hydrogenation reactor. A $H_2$-rich stream can be recovered via another absorption tower. The liquid stream from the second absorption tower can be recycled to the flash drum, and portions of the liquid hydrocarbons can be used as absorbents for the two absorption towers. This embodiment shows an additional aspect where $C_{2+}$ hydrocarbons can be separated from a stream that is enriched in $H_2$.

Figure 14:
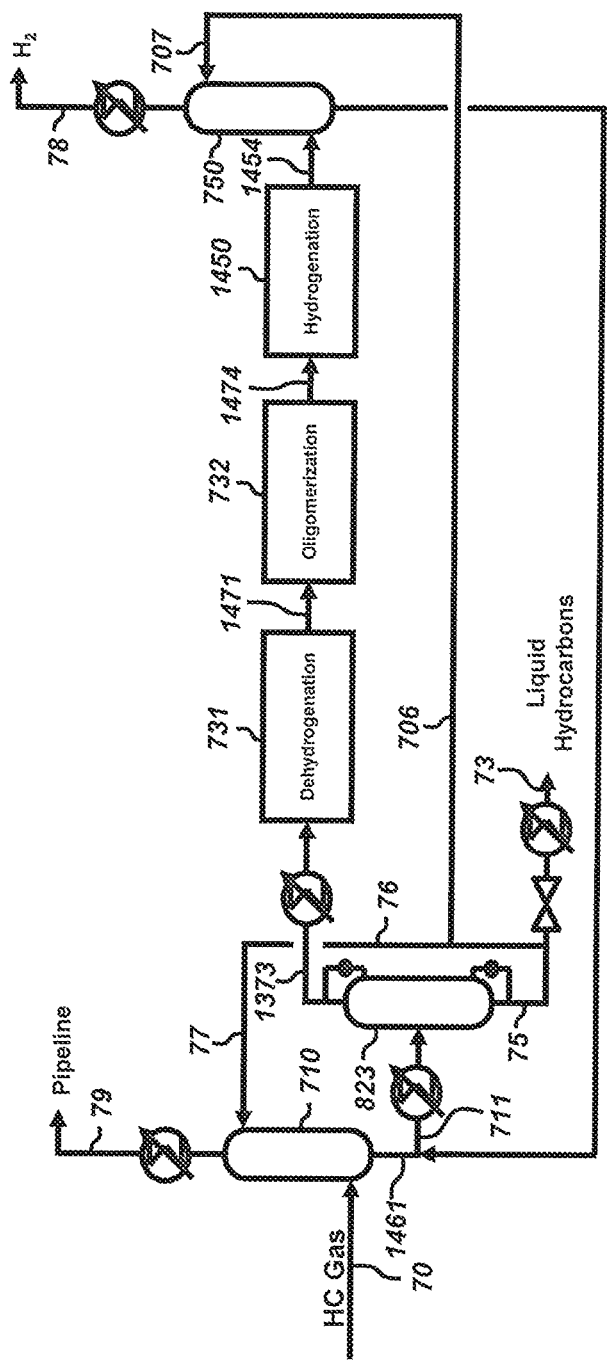
FIG. 14 depicts a flow diagram of another illustrative NGL upgrading system, according to or more embodiments provided herein, wherein a shale gas stream passes through an absorption tower followed by a distillation column, a $CH_4$-rich stream is recovered as a gas stream from the absorption tower and delivered to the pipeline, liquid hydrocarbons are recovered as a liquid product from the distillation column, the gas stream from the distillation column passes through a reactor sequence can include a dehydrogenation reactor, an oligomerization reactor, a hydrogenation reactor and a $H_2$-rich stream is recovered via another absorption tower, the liquid stream from the second absorption tower is recycled to the distillation column, and portions of the liquid hydrocarbons are used as absorbents for the two absorption towers.

FIG. 14 depicts a flow diagram of another illustrative NGL upgrading system in which a shale gas stream passes through an absorption tower followed by a distillation column. A $CH_4$-rich stream can be recovered as a gas stream from the absorption tower and delivered to the pipeline. Liquid hydrocarbons can be recovered as a liquid product from the distillation column. The gas stream from the distillation column can flow through a reactor sequence that includes a dehydrogenation reactor, an oligomerization reactor, and a hydrogenation reactor. A $H_2$-rich stream can be recovered via another absorption tower, the liquid stream from the second absorption tower can be recycled to the distillation column, and portions of the liquid hydrocarbons can be used as absorbents for the two absorption towers.

Figure 15:
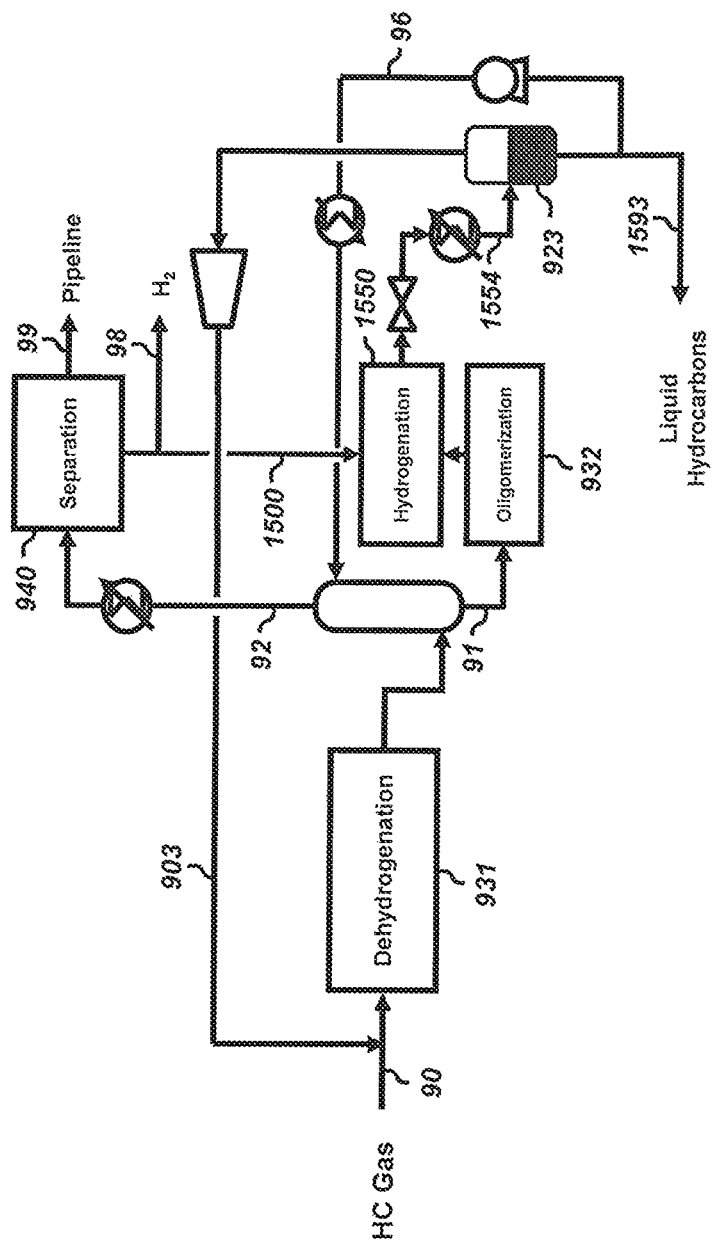
FIG. 15 depicts a flow diagram of another illustrative NGL upgrading system, according to or more embodiments provided herein, wherein a shale gas stream passes through a dehydrogenation reactor, a $CH_4$-containing stream is recovered via an absorption tower, a $CH_4$-rich stream is delivered to the pipeline after $H_2$ is recovered, the remaining stream from the absorption tower passes through an oligomerization reactor, then through a hydrogenation reactor which is also fed with a portion of the $H_2$-rich stream, and the product from the hydrogenation reactor is separated via a flash drum, the gas stream from the flash drum is recycled back to the dehydrogenation reactor and a portion of the liquid hydrocarbons is used as the absorbent of the absorption tower.

FIG. 15 depicts a flow diagram of another illustrative NGL upgrading system, in which a shale gas stream passes through a dehydrogenation reactor. A $CH_4$-containing stream can be recovered via an absorption tower, and a $CH_4$-rich stream can be delivered to the pipeline after $H_2$ is recovered. The remaining stream from the absorption tower can flow through an oligomerization reactor, then through a hydrogenation reactor which is also fed with a portion of the $H_2$-rich stream. The product from the hydrogenation reactor can be separated via a flash drum, the gas stream from the flash drum can be recycled back to the dehydrogenation reactor and a portion of the liquid hydrocarbons can be used as the absorbent of the absorption tower.

Figure 16:
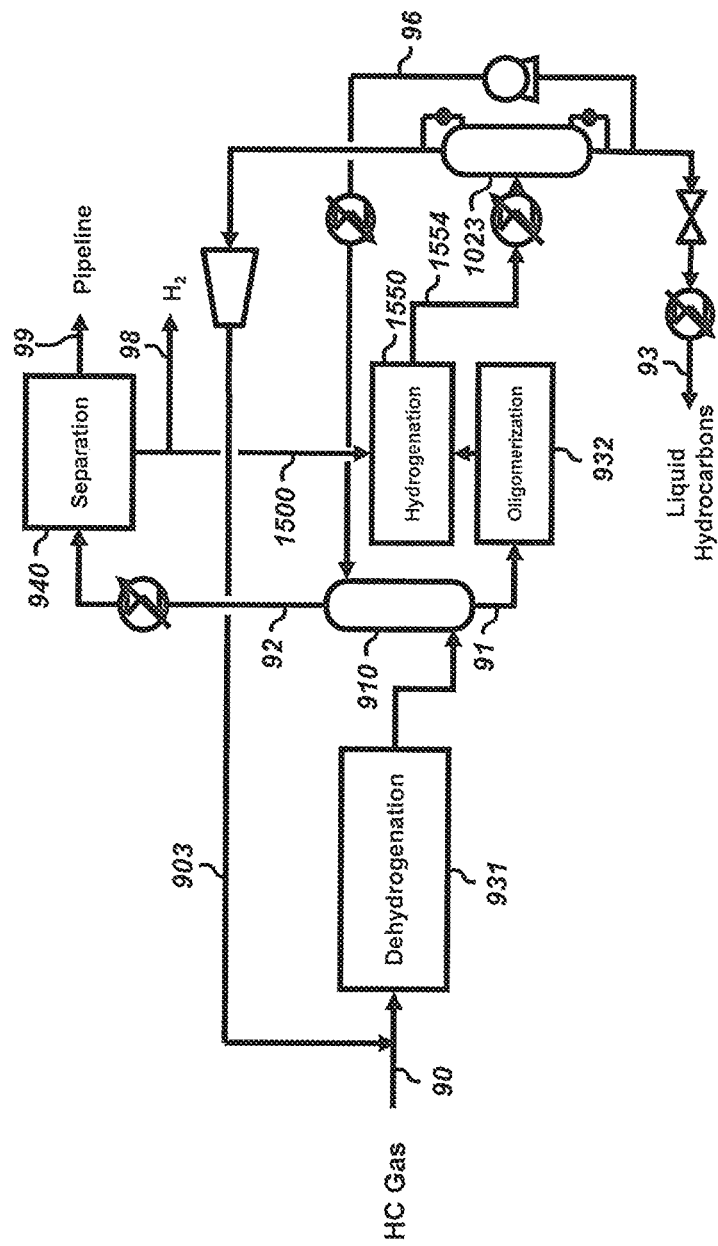
FIG. 16 depicts a flow diagram of another illustrative NGL upgrading system, according to or more embodiments provided herein, wherein a shale gas stream passes through a dehydrogenation reactor, a $CH_4$-containing stream is recovered via an absorption tower, a $CH_4$-rich stream is delivered to the pipeline after $H_2$ is recovered, the remaining stream from the absorption tower passes through an oligomerization reactor, then through a hydrogenation reactor which is also fed with a $H_2$-rich stream and the product from the hydrogenation reactor is separated via a distillation column, the vapor stream from the distillation column is recycled back to the dehydrogenation reactor and a portion of the liquid hydrocarbons stream is used as the absorbent of the absorption tower.
Figure 17:
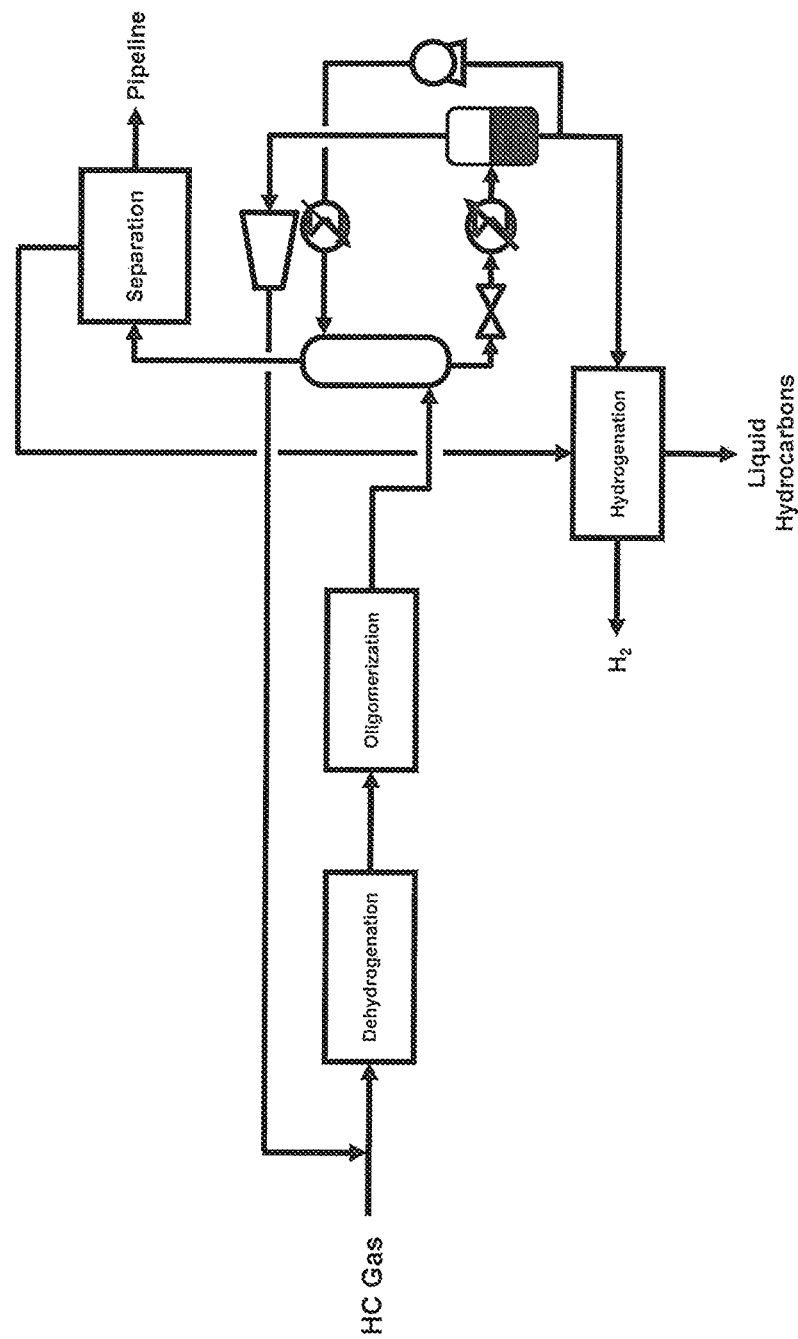
FIG. 17 depicts a flow diagram of another illustrative NGL upgrading system, according to or more embodiments provided herein, wherein a shale gas stream passes through a dehydrogenation reactor followed by an oligomerization reactor, the liquid hydrocarbons are recovered as the product via an absorption tower followed by a flash separation, the $CH_4$-containing stream from the absorption tower is delivered to the pipeline after $H_2$ is separated, the gas from the flash drum is recycled to the dehydrogenation reactor, a portion of the liquid hydrocarbon stream is used as the absorbent for the absorption tower and the second portion passes through a hydrogenation reactor which is also fed with a $H_2$-rich stream to produce hydrogenated liquid product stream.
Figure 18:
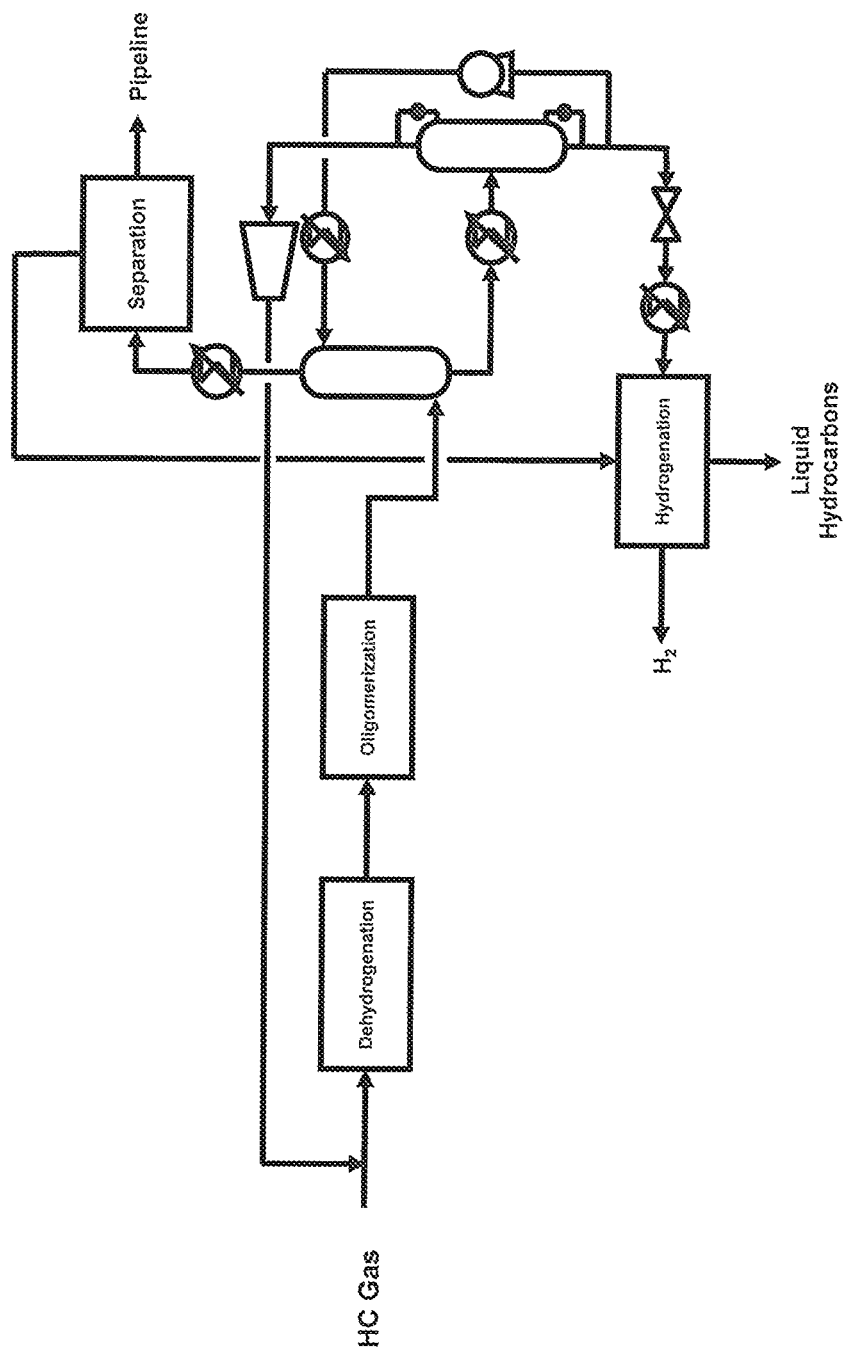
FIG. 18 depicts a flow diagram of another illustrative NGL upgrading system, according to or more embodiments provided herein, wherein a shale gas stream passes through a dehydrogenation reactor followed by an oligomerization reactor, the liquid hydrocarbons are recovered as the product via an absorption tower followed by a distillation column, the $CH_4$-containing stream from the absorption tower is delivered to the pipeline after $H_2$ is separated, the gas from the distillation column is recycled to the dehydrogenation reactor, a portion of the liquid hydrocarbon stream is used as the absorbent for the absorption tower and the second portion passes through a hydrogenation reactor which is also fed with a $H_2$-rich stream to produce hydrogenated liquid product stream.
Figure 19:
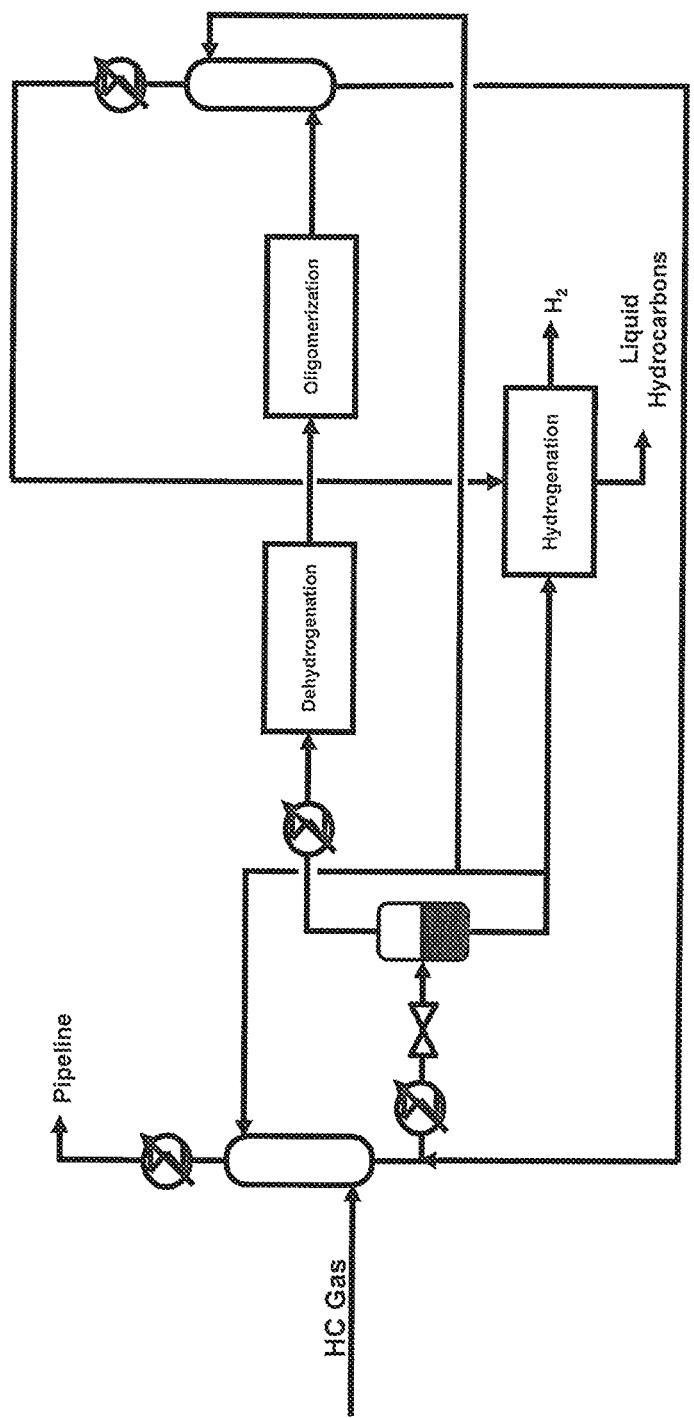
FIG. 19 depicts a flow diagram of another illustrative NGL upgrading system, according to or more embodiments provided herein, wherein a shale gas stream is separated via an absorption tower followed by a flash separation, the $CH_4$-containing stream from the absorption tower is delivered to the pipeline, the gas from the flash drum passes through a dehydrogenation reactor followed by an oligomerization reactor and is separated via another absorption tower, the liquid stream from this absorption tower is recycled to the flash drum, and portions of the liquid hydrocarbons stream are used as the absorbents for the two absorption towers and the remaining liquid hydrocarbons pass through a hydrogenation reactor which is also fed with a $H_2$-rich stream to produce hydrogenated liquid product stream.
Figure 20:
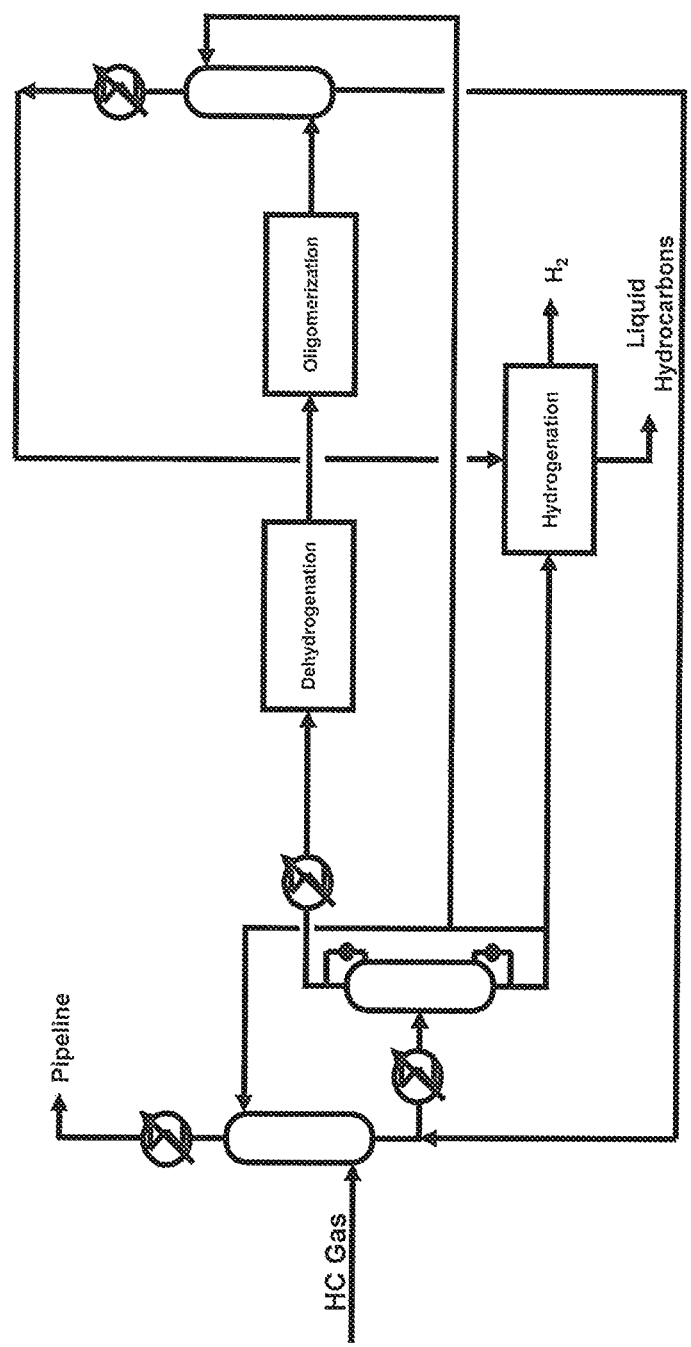
FIG. 20 depicts a flow diagram of another illustrative NGL upgrading system, according to or more embodiments provided herein, wherein a shale gas stream is separated via an absorption tower followed by a distillation column, the $CH_4$-containing stream from the absorption tower is delivered to the pipeline, the gas from the distillation column passes through a dehydrogenation reactor followed by an oligomerization reactor and is separated via another absorption tower, the liquid stream from this absorption tower is recycled to the distillation column, and portions of the liquid hydrocarbons stream are used as the absorbents for the two absorption towers and the remaining liquid hydrocarbons pass through a hydrogenation reactor which is also fed with a $H_2$-rich stream to produce hydrogenated liquid product stream.
Figure 21:
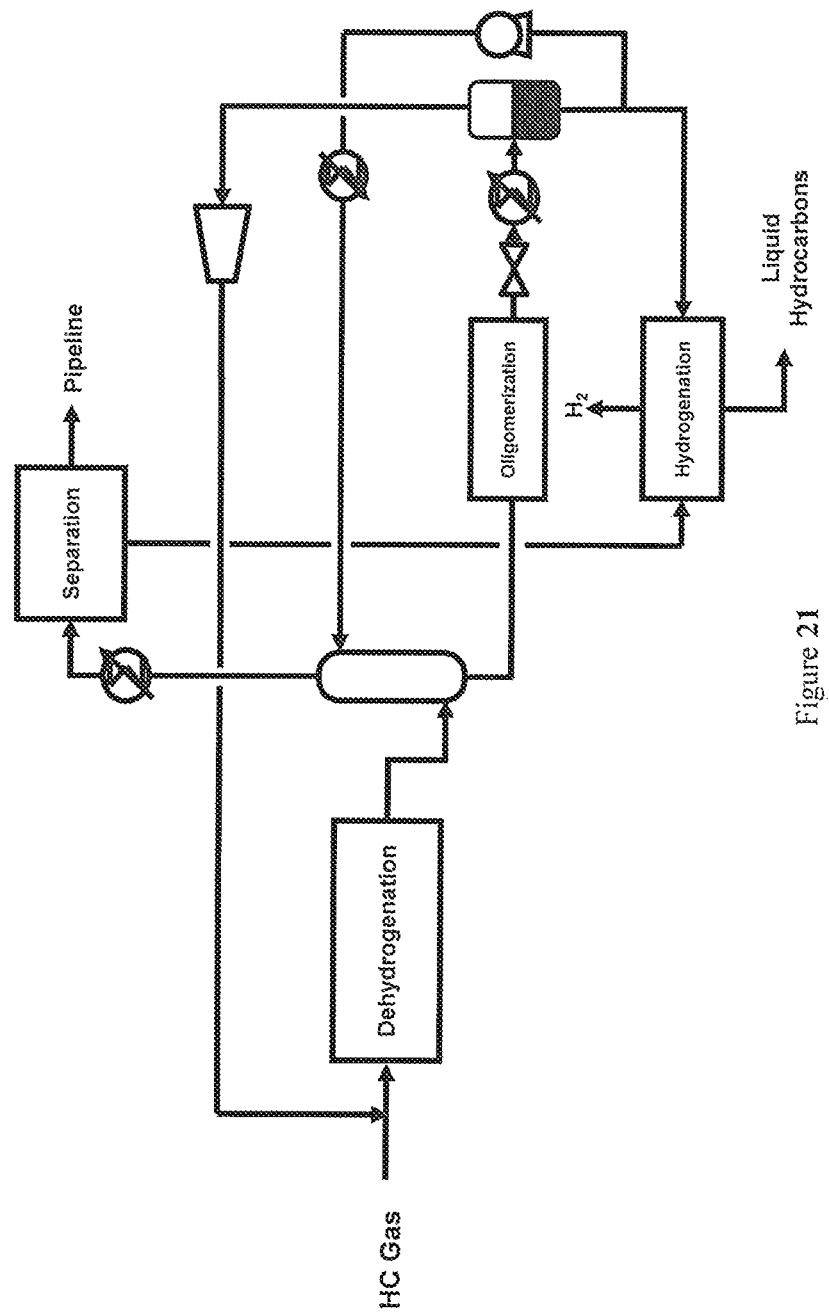
FIG. 21 depicts a flow diagram of another illustrative NGL upgrading system, according to or more embodiments provided herein, wherein a shale gas stream passes through a dehydrogenation reactor, a $CH_4$-containing stream is recovered via an absorption tower, a $CH_4$-rich stream is delivered to the pipeline after $H_2$ is recovered, the remaining stream from the absorption tower passes through an oligomerization reactor and is separated via a flash drum, the gas stream from the flash drum is recycled back to the dehydrogenation reactor and a portion of the liquid hydrocarbon stream is used as the absorbent for the absorption tower and the second portion passes through a hydrogenation reactor which is also fed with a $H_2$-rich stream to produce hydrogenated liquid product stream.
Figure 22:
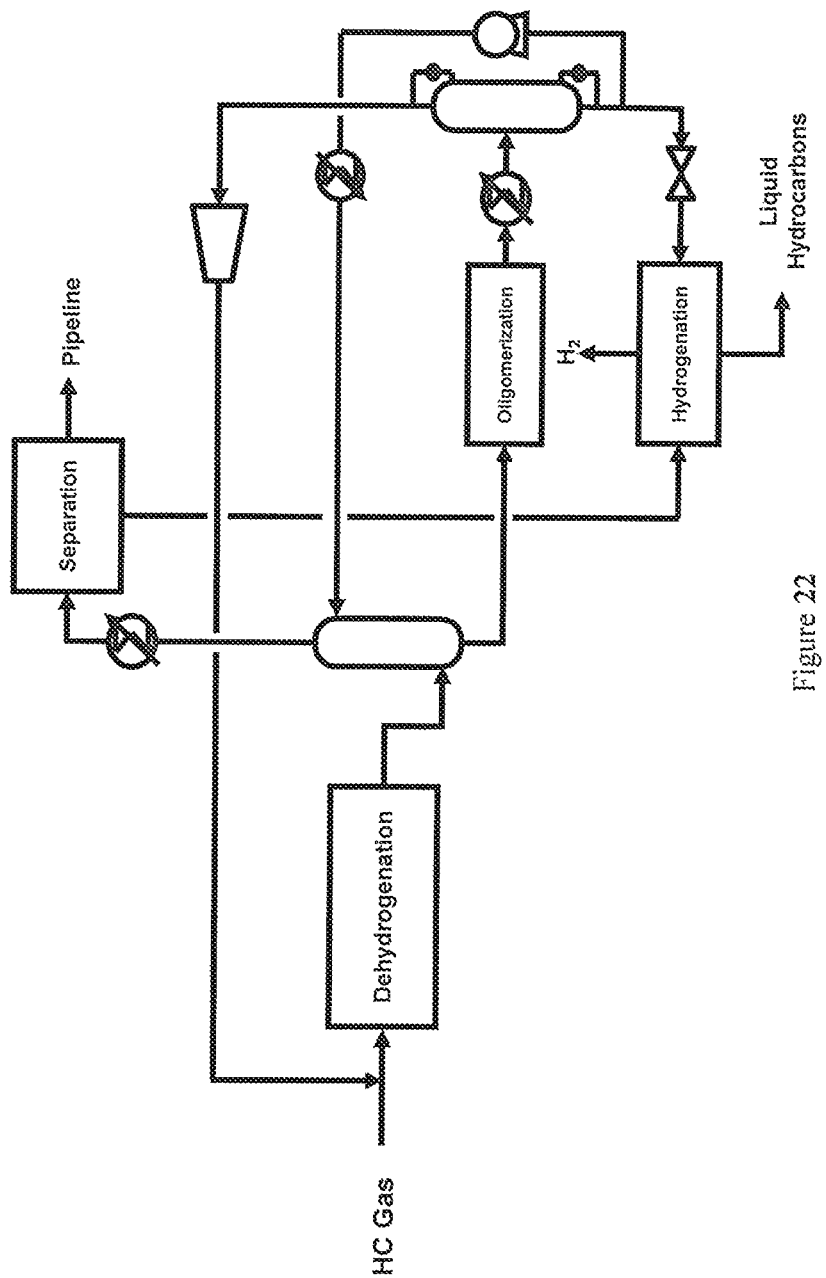
FIG. 22 depicts a flow diagram of another illustrative NGL upgrading system, according to or more embodiments provided herein, wherein a shale gas stream passes through a dehydrogenation reactor, a $CH_4$-containing stream is recovered via an absorption tower, a $CH_4$-rich stream is delivered to the pipeline after $H_2$ is recovered, the remaining stream from the absorption tower passes through an oligomerization reactor and is separated via a distillation column, the gas stream from the distillation column is recycled back to the dehydrogenation reactor and a portion of the liquid hydrocarbon stream is used as the absorbent for the absorption tower and the second portion passes through a hydrogenation reactor which is also fed with a $H_2$-rich stream to produce hydrogenated liquid product stream.
Figure 23:
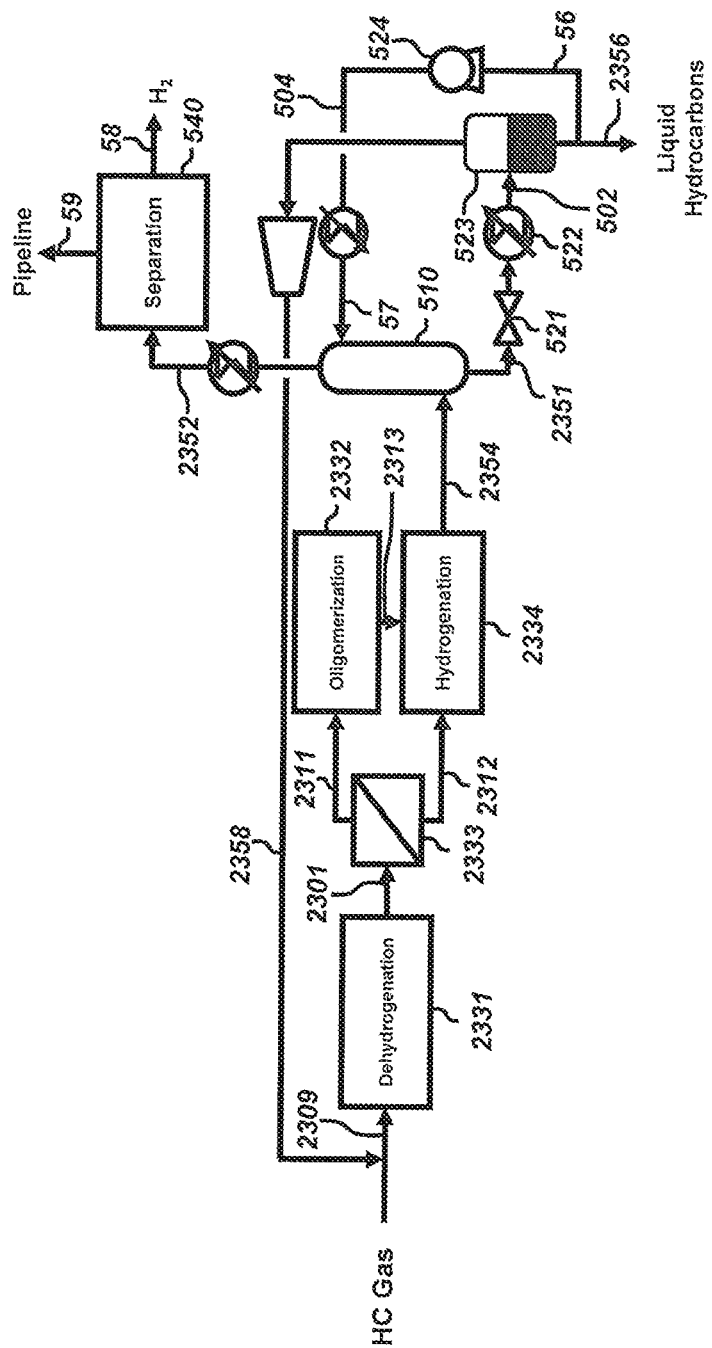
FIG. 23 depicts a flow diagram of another illustrative NGL upgrading system, according to or more embodiments provided herein, wherein a shale gas stream passes through an upgrading process can include a dehydrogenation reactor, a membrane separation, an oligomerization reactor, and a hydrogenation reactor, the liquid hydrocarbons are recovered as the product via an absorption tower followed by a flash separation, the $CH_4$-containing stream from the absorption tower is delivered to the pipeline after $H_2$ is separated, the gas from the flash drum is recycled to the dehydrogenation reactor, and a portion of the liquid hydrocarbons is used as the absorbent of the absorption tower.

FIG. 16 depicts a flow diagram of another illustrative NGL upgrading system, in which a shale gas stream passes through a dehydrogenation reactor, a $CH_4$-containing stream is recovered via an absorption tower, a $CH_4$-rich stream is delivered to the pipeline after $H_2$ is recovered, the remaining stream from the absorption tower passes through an oligomerization reactor, then through a hydrogenation reactor which is also fed with a $H_2$-rich stream and the product from the hydrogenation reactor is separated via a distillation column. The vapor stream from the distillation column can be recycled back to the dehydrogenation reactor and a portion of the liquid hydrocarbons stream can be used as the absorbent of the absorption tower.

FIGS. 17 through 22 depicts yet another set of embodiments. They are similar to those in FIGS. 11 through 16 in that these systems use a three-step upgrading process containing dehydrogenation, oligomerization, and hydrogenation. The only difference is that in these embodiments, the hydrogenation reaction takes place after liquid hydrocarbons are separated from the stream exiting the oligomerization reactor using the absorption unit. Also this set of embodiments are synthesized from the embodiments in FIG. 5 through 10 by just adding a hydrogenation reaction unit after recovery of the liquid hydrocarbon products and the $H_2$-rich stream feed to the hydrogenation reactor. One benefit of doing so is to avoid hydrogenating unconverted NGL alkene derivatives. Again, any other configuration that can be synthesized by rearranging the processing units of the embodiments mentioned in this invention is also included in this invention.

FIG. 23 through 26 depict alternative flow diagrams of a four-step upgrading process that utilizes dehydrogenation, oligomerization, membrane separation and hydrogenation. For example, in FIG. 23, a natural gas stream 2309 can enter a dehydrogenation reactor 2331 to provide an at least partially dehydrogenated stream 2301 that can be fed to a membrane separation unit 2333. The outlet stream 2311 on the retentate side can contain mainly $C_{2+}$ hydrocarbons and the outlet stream 2312 on the permeate side can be a $H_2$-rich stream. Stream 2311 can flow through an oligomerization reactor 2332 in which a portion of the $C_{2+}$ alkenes can be converted to one or more heavier alkenes. The outlet stream 2313 of this oligomerization reactor 2313 can be fed to a hydrogenation reactor 2334 which uses the $H_2$-rich stream 2312 as the source of hydrogen. In the hydrogenation reactor 2334, $C_{2+}$ alkenes can react with $H_2$ to yield alkane derivatives thereof. The hydrogenated stream 2354 exiting the hydrogenation reactor 2334 can pass through a two-step separation, such as that depicted in FIG. 5. Anywhere from 1% to 99% of the liquid hydrocarbons in product stream 2356 can be fed to the absorption tower 510 as the absorbent. In some cases, the amount of the liquid hydrocarbons that is recycled to the absorption tower 510 can range from a low of about 1%, about 3%, about 5%, about 10%, or about 15% to a high of about 15%, about 50%, about 75%, about 95%, or about 95%.

Figure 24:
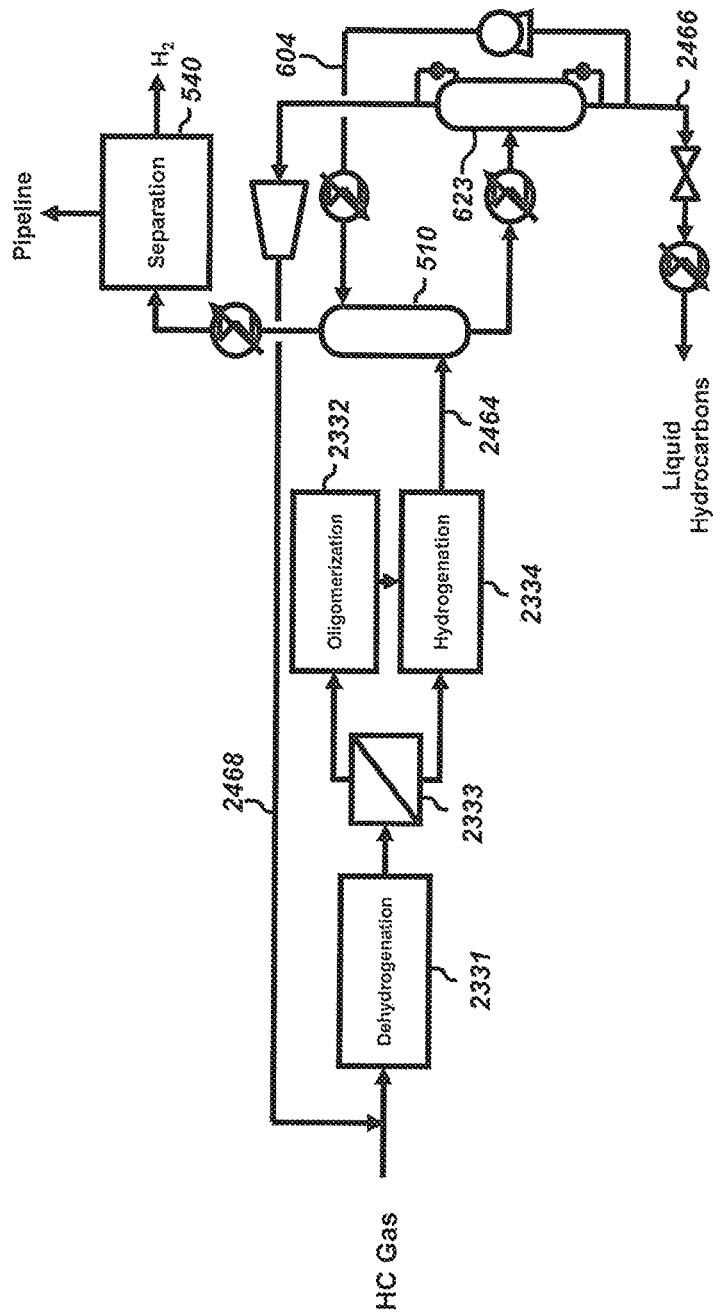
FIG. 24 depicts a flow diagram of another illustrative NGL upgrading system, according to or more embodiments provided herein, wherein a shale gas stream passes through a reactor sequence can include a dehydrogenation reactor, a membrane separation, an oligomerization reactor, and a hydrogenation reactor, the liquid hydrocarbons are recovered as the product via an absorption tower followed by a distillation column, the $CH_4$-containing stream from the absorption tower is delivered to the pipeline after $H_2$ is separated, the gas from the distillation column is recycled to the dehydrogenation reactor, and a portion of the liquid hydrocarbons is used as the absorbent of the absorption tower.

FIG. 24 depicts a flow diagram of another illustrative NGL upgrading system, wherein a shale gas stream passes through a reactor sequence that includes a dehydrogenation reactor 2331, a membrane separation 2333, an oligomerization reactor 2332, and a hydrogenation reactor 2334. The liquid hydrocarbons in stream 2464 can be recovered as the product via an absorption tower 510 followed by a distillation column 623. The $CH_4$-containing stream from the absorption tower 510 can be delivered to the pipeline after $H_2$ is separated in separator 540. The gas from the distillation column 610 can be recycled to the dehydrogenation reactor 2331 via recycle stream 2468, and a portion of the liquid hydrocarbons 2466 can be used as the absorbent via stream 604 for the absorption tower 510. Anywhere from 1% to 99% of the liquid hydrocarbons via stream 604 can be fed to the absorption tower 510 as the absorbent. In some cases, the amount of the liquid hydrocarbons that is recycled to the absorption tower 510 can range from a low of about 1%, about 3%, about 5%, about 10%, or about 15% to a high of about 15%, about 50%, about 75%, about 95%, or about 95%.

Figure 25:
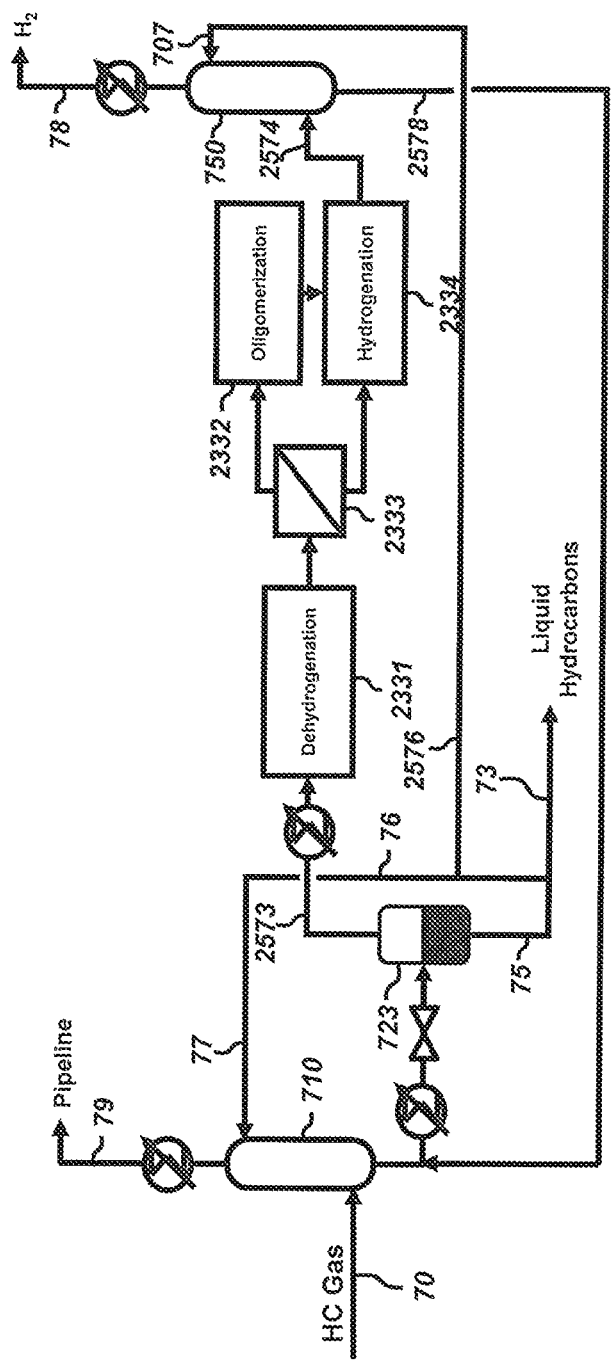
FIG. 25 depicts a flow diagram of another illustrative NGL upgrading system, according to or more embodiments provided herein, wherein the shale gas stream is separated via an absorption tower followed by a flash separation, the $CH_4$-rich stream from the absorption tower is delivered to the pipeline, the gas from the flash drum passes through a reactor sequence can include a dehydrogenation reactor, a membrane separation, an oligomerization reactor, and a hydrogenation reactor and is separated via another absorption tower, the liquid stream from this absorption tower is recycled to the flash drum, and portions of the liquid hydrocarbons are used as absorbents of the two absorption towers.

FIG. 25 depicts a flow diagram for another illustrative NGL upgrading system. As first described with reference to FIG. 7, the shale gas stream 70 can be separated via the first absorption tower 723 followed by the flash separation 723. The $CH_4$-rich stream 79 from the first absorption tower 723 can be delivered to a pipeline. The gas steam 2573 from the flash drum 723 can flow through a reactor sequence that includes the dehydrogenation reactor 2331, the membrane separation 2333, the oligomerization reactor 2332, and the hydrogenation reactor 2334. The effluent 2574 from the foregoing reactor sequence can be further separated via the second absorption tower 750 where $H_2$ can separated from the $C_{2+}$ hydrocarbons. The gas stream 78 mainly contains $H_2$ and the liquid stream 2578 mainly contains $C_{2+}$ hydrocarbons. The liquid stream 2578 can be recycled to the flash drum 723, and portions of the liquid hydrocarbons can be used as absorbents for either or both of the absorption towers 710, 750.

Anywhere from 1% to 99% of the liquid hydrocarbons exiting the flash drum 723 can be fed to either one or both absorption towers 710, 750 as the absorbent. In some cases, the amount of the liquid hydrocarbons that is recycled to either one or both absorption towers 710, 750 can range from a low of about 1%, about 3%, about 5%, about 10%, or about 15% to a high of about 15%, about 50%, about 75%, about 95%, or about 95%.

Figure 26:
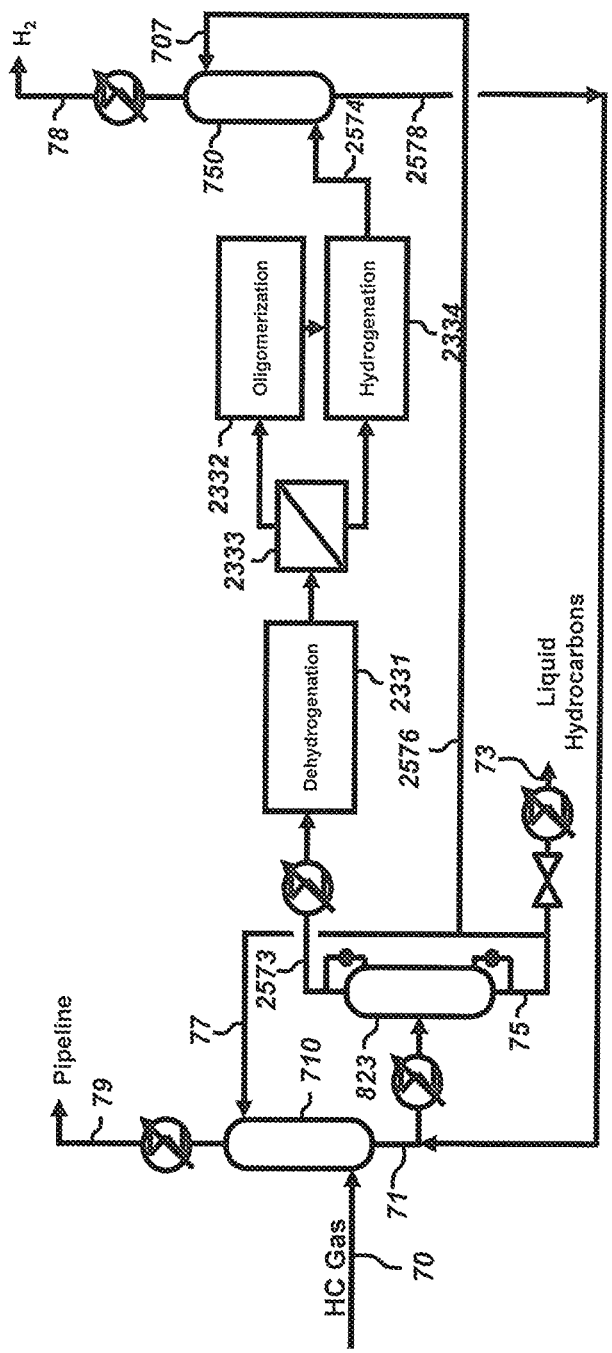
FIG. 26 depicts a flow diagram of another illustrative NGL upgrading system, according to or more embodiments provided herein, wherein a shale gas stream is separated via an absorption tower followed by a distillation column, the $CH_4$-rich stream from the absorption tower is delivered to the pipeline, the gas from the distillation column passes through a reactor sequence can include a dehydrogenation reactor, a membrane separation, an oligomerization reactor, and a hydrogenation reactor and is separated via another absorption tower, the liquid stream from this absorption tower is recycled to the distillation column, and portions of the liquid hydrocarbons are used as absorbents of the two absorption towers.

FIG. 26 depicts a flow diagram for another illustrative NGL upgrading system, wherein the shale gas stream can be separated via the first absorption tower 710 followed by distillation separator 823. Referring to FIGS. 8 and 26, the $CH_4$-rich stream 79 from the first absorption tower 710 can be delivered to the pipeline. The gas in stream 2573 from the distillation column 823 can flow to the dehydrogenation reactor 2331, the membrane separation 2333, the oligomerization reactor 2332, and the hydrogenation reactor 2331. The processed and converted stream 2574 can be separated via the second absorption tower 750. The liquid stream 2578 from this second absorption tower 750 can be recycled to the distillation column 823.

Portions of the liquid hydrocarbons from the column 823 can be used as the absorbent (via streams 77, 707) for either one or both absorption towers 710, 750. Anywhere from 1% to 99% of the liquid hydrocarbons exiting the column 823 can be fed to either one or both absorption towers 710, 750 as the absorbent. In some cases, the amount of the liquid hydrocarbons that is recycled to either one or both absorption towers 710, 750 can range from a low of about 1%, about 3%, about 5%, about 10%, or about 15% to a high of about 15%, about 50%, about 75%, about 95%, or about 95%.

In any of the embodiments provided above, the stream(s) exiting a dehydrogenation unit/reactor (230, 331, 430, 531, 631, 731, 931, 2331) can contain greater than about 50 mol % olefins, such as greater than about 60 mol % olefins or greater than about 75 mol % olefins. For example, these stream exiting a dehydrogenation unit/reactor can contain one or more C2 to C12 olefins in amounts ranging from a low of about 50 mol %, 60 mol % or 65 mol % to a high of about 70 mol %, 85 mol % or 100 mol %, based on the total feed stream. Such stream(s) also can include up to 80 mol % alkanes, for example, methane, ethane, propane, butane, and pentane; although the alkane generally comprises less than about 50 mol % of the stream, and preferably less than about 20 mol % of the stream.

The stream(s) can have a temperature of 250° C. or higher. For example, the temperature can range from a low of about 250°, 450° C., or 500° to a high of about 550° C., 600° C., or 700° C. The temperature also can be 420° C. or higher, 450° C. or higher, 480° C. or higher, 500° C. or higher, 525° C. or higher, 550° C. or higher, 560° C. or higher, 570° C. or higher, or 575° C. or higher, or 600° C. or higher.

The resulting oligomer stream exiting an oligomerization unit/reactor (e.g. streams 220, 332, 420, 532, 632, 732, 932, 2332) can be or can include one or more olefins having from 4 to 26 carbon atoms, such as 12 to 20 carbon atoms, or 16 to 20 carbon atoms. The resulting oligomers, for example, can include butene, hexene, octene, decene, dodecene, tetradecane, hexadecane, octadecene and eicosene and higher olefins, as well as any combinations thereof. The resulting oligomer(s) also can have less than about 5% aromatics and less than about 10 ppm sulfur. The resulting oligomer(s) also can have zero or substantially no aromatics and zero or substantially no sulfur.

The resulting oligomer(s) are useful as precursors, feedstocks, monomers and/or comonomers for various commercial and industrial uses including polymers, plastics, rubbers, elastomers, as well as chemicals. For example, these resulting oligomer(s) are also useful for making polybutene-1, polyethylene, polypropylene, polyalpha olefins, block copolymers, detergents, alcohols, surfactants, oilfield chemicals, solvents, lubricants, plasticizers, alkyl amines, alkyl succinic anhydrides, waxes, and many other specialty chemicals.

The resulting oligomer(s) are especially useful for production of diesel and jet fuels, or as a fuel additive. In certain embodiments, the resulting oligomer(s) can have a boiling point in the range of 170° C. to 360° C. and more particularly 200° C. to 300° C. The resulting oligomer(s) also can have a Cetane Index (CI) of 40 to 100 and more particularly 65 to 100. The resulting oligomer(s) also can have a pour point of −50° C. or −40° C.

The resulting hydrogenated streams exiting a hydrogenation unit/reactor 1150, 1350, 1450, 1550, 2334 (e.g. stream(s) 1154, 1354, 1454, 1554, 2354) can be or can include one or more alkanes having from 4 to 26 carbon atoms, such as 12 to 20 carbon atoms, or 16 to 20 carbon atoms. The resulting alkanes, for example, can include butane, hexane, octane, decane, dodecane, tetradecane, hexadecane, octadecane and eicosane and higher olefins, as well as any combinations thereof. The resulting alkane(s) also can have less than about 5% aromatics and less than about 10 ppm sulfur. The resulting oligomer(s) also can have zero or substantially no aromatics and zero or substantially no sulfur. Referring to FIGS. 4-26, certain stream compositions are provided in Table 2 below.

TABLE 2

Compositions of streams depicted in FIGS. 4-26.

| | 40 | 50 | 51 | 52 | 54 | 55 | 60 | 61 | 62 |
|---|---|---|---|---|---|---|---|---|---|
| H2 | 0 | 0 | <5 | >20 | 0-50 | <1 | 0 | <5 | >20 |
| CH4 | 50-95 | 50-95 | <5 | >50 | 30-95 | <1 | 50-95 | <5 | >50 |
| C2-C5 paraffin | 5-50 | 5-50 | 5-95 | <5 | 5-50 | <5 | 5-50 | 5-95 | <5 |
| C5+ paraffin | 0-10 | 0-10 | 0-10 | <1 | 0-10 | 10-50 | 0-10 | 0-10 | <1 |

TABLE 2-continued

Compositions of streams depicted in FIGS. 4-26.

| | | | | | | | | |
|---|---|---|---|---|---|---|---|---|
| C2-C5 olefin | 0 | 0 | 5-95 | <5 | 0-50 | <5 | 0 | 5-95 | <5 |
| C5+ olefin | 0 | 0 | 5-80 | <1 | 0-30 | 50-90 | 0 | 5-80 | <1 |

| | 64 | 65 | 70 | 71 | 73 | 74 | 75 | 78 | 79 |
|---|---|---|---|---|---|---|---|---|---|
| H2 | 0-50 | <1 | 0 | <5 | <1 | 0-80 | <1 | >90 | <1 |
| CH4 | 30-95 | <1 | 50-95 | <5 | <1 | <5 | <1 | <5 | >95 |
| C2-C5 paraffin | 5-50 | <5 | 5-50 | 5-95 | <5 | 5-50 | <5 | <5 | <5 |
| C5+ paraffin | 0-10 | 10-50 | 0-10 | 0-10 | 50-90 | 0-10 | 10-50 | <1 | <1 |
| C2-C5 olefin | 0-50 | <5 | 0 | 5-95 | <5 | 0-80 | <5 | <5 | <5 |
| C5+ olefin | 0-30 | 50-90 | 0 | 5-80 | 10-50 | 0-80 | 50-90 | <1 | <1 |

| | 90 | 91 | 92 | 93 | 501 | 601 | 701 | 703 | 708 |
|---|---|---|---|---|---|---|---|---|---|
| H2 | 0 | <5 | >20 | <1 | 0-35 | 0-35 | 0-35 | <5 | <5 |
| CH4 | 50-95 | <5 | >50 | <1 | 30-95 | 30-95 | <5 | <5 | <5 |
| C2-C5 paraffin | 5-50 | 5-95 | <5 | <5 | 5-50 | 5-50 | 5-80 | 5-95 | 5-95 |
| C5+ paraffin | 0-10 | 0-10 | <1 | 10-50 | 0-10 | 0-10 | 0-10 | <10 | 0-10 |
| C2-C5 olefin | 0 | 5-95 | <5 | <5 | 5-50 | 5-50 | 5-80 | 5-95 | 5-95 |
| C5+ olefin | 0 | 5-80 | <1 | 50-90 | 0-10 | 0-10 | 0-10 | <10 | 5-80 |

| | 803 | 808 | 903 | 1103 | 1153 | 1154 | 1161 | 1203 | 1253 |
|---|---|---|---|---|---|---|---|---|---|
| H2 | <5 | <5 | <5 | <10 | <1 | 0-50 | <5 | <10 | <1 |
| CH4 | <5 | <5 | <5 | <10 | <1 | 30-95 | <5 | <10 | <1 |
| C2-C5 paraffin | 5-95 | 5-95 | 50-90 | 50-90 | <5 | 5-50 | 5-95 | 50-90 | <5 |
| C5+ paraffin | <10 | 0-10 | <5 | <10 | 50-90 | 0-30 | 5-95 | <10 | 50-90 |
| C2-C5 olefin | 5-95 | 5-95 | 50-90 | 50-90 | <5 | 0-50 | 5-95 | 50-90 | <5 |
| C5+ olefin | <10 | 5-80 | <5 | <10 | 10-50 | 0-30 | 5-95 | <10 | 10-50 |

| | 1354 | 1358 | 1373 | 1454 | 1461 | 1471 | 1474 | 1500 | 1554 |
|---|---|---|---|---|---|---|---|---|---|
| H2 | 5-50 | <5 | <5 | 5-50 | <5 | 5-50 | 5-50 | >90 | <5 |
| CH4 | <5 | <5 | <5 | <5 | <5 | <5 | <5 | <5 | <5 |
| C2-C5 paraffin | 5-95 | 5-95 | 5-95 | 5-95 | 5-95 | 5-95 | 5-95 | <5 | 5-95 |
| C5+ paraffin | 5-95 | 5-95 | <10 | 5-95 | 5-95 | 5-95 | 5-95 | <1 | 5-95 |
| C2-C5 olefin | 5-95 | 5-95 | 5-95 | 5-95 | 5-95 | 5-95 | 5-95 | <5 | 5-95 |
| C5+ olefin | 5-95 | 5-95 | <10 | 5-95 | 5-95 | 5-95 | 5-95 | <1 | 5-95 |

| | 1593 | 2301 | 2309 | 2311 | 2312 | 2313 | 2351 | 2352 | 2354 |
|---|---|---|---|---|---|---|---|---|---|
| H2 | <1 | 0-35 | 0-35 | 0-20 | >80 | 5-50 | <5 | 5-50 | 0-30 |
| CH4 | <1 | 30-95 | 30-95 | 30-95 | <20 | 5-50 | <5 | 5-80 | 30-95 |
| C2-C5 paraffin | <5 | 5-50 | 5-50 | 5-50 | <20 | 5-95 | 5-95 | <5 | 5-50 |
| C5+ paraffin | 50-90 | 0-10 | 0-10 | 0-10 | <20 | 5-95 | 5-95 | <5 | 0-30 |
| C2-C5 olefin | <5 | 5-50 | 5-50 | 5-50 | <20 | 5-95 | 5-95 | <5 | 0-50 |
| C5+ olefin | 10-50 | 0-10 | 0-10 | 0-10 | <20 | 5-95 | 5-95 | <5 | 0-30 |

| | 2356 | 2358 | 2464 | 2466 | 2468 | 2573 | 2576 | 2574 | 2578 |
|---|---|---|---|---|---|---|---|---|---|
| H2 | <1 | <5 | 0-30 | <1 | <5 | <1 | <1 | 5-50 | <5 |
| CH4 | <1 | <5 | 30-95 | <1 | <5 | <1 | <1 | <5 | <5 |
| C2-C5 paraffin | <5 | 5-95 | 5-50 | <5 | 5-95 | 5-95 | <5 | 5-95 | 5-95 |
| C5+ paraffin | 50-90 | 5-95 | 0-30 | 50-90 | 5-95 | <5 | 50-90 | 5-95 | 5-95 |
| C2-C5 olefin | <5 | 5-95 | 0-50 | <5 | 5-95 | 5-95 | <5 | 5-95 | 5-95 |
| C5+ olefin | 10-50 | 5-95 | 0-30 | 10-50 | 5-95 | <5 | 10-50 | 5-95 | 5-95 |

Systems and processes for upgrading natural gas liquids (NGL) into one or more liquid hydrocarbon products have been provided above. It should be apparent from the foregoing description that detailed embodiments can be adjusted for different desired liquid hydrocarbon products, different upgrading processes, different separation techniques, different operating scales, and for scenarios where only a portion of the NGLs in a hydrocarbon stream is upgraded into liquid hydrocarbons.

Prophetic Examples

The foregoing discussion can be further described with reference to the following non-limiting prophetic examples. Process simulation results are provided for the processes described above with specific reference to the processing configuration shown in FIGS. 3, 5 and 6. The process simulation was implemented by Aspen Plus. The feed information, including composition, flowrate, temperature and pressure, were the same for all three simulations. The conversion in the dehydrogenation reactors of all three processes were set to be 90% of the equilibrium value. The oligomerization reactors were set to the same equilibrium conversion. The performance of all three simulations are summarized in Table 2.

Operating conditions and stream information for simulations 1-4 are summarized in Tables 3-6 below. Simulations 1 and 2 are comparative simulations. Simulations 3 and 4 represent the inventive embodiments described herein. In Simulation 1, the pressure of the dehydrogenation reactor is 5 bar and the overall liquid hydrocarbon yield is 79.68%. In Simulation 2, the pressure of the dehydrogenation reactor is increased to 29 bar and the overall liquid hydrocarbon yield is 63.12%. The higher pressure dehydrogenation reactor decreases the overall liquid hydrocarbon yield. However, the inventive Simulations 3 and 4 show high liquid hydrocarbon yield even when the dehydrogenation reactors are operated at the higher pressure of 29 bar. It appears the absorption tower 510, 610 and liquid hydrocarbon as the absorbent 57, 67 can provide better separation between $CH_4$ (or $H_2$) and $C_{2+}$; hence, the $C_{2+}$ loss is decreased and the liquid hydrocarbon yield is increased. From these simulation results, it can be concluded that the processes described herein, which utilize an absorption tower and olefin recycle as the absorbent, can provide significantly higher yields of the desired products, even at higher dehydrogenation pressures.

TABLE 3

Performance of All Simulated Embodiments

| | FIG. No. | Pressure of Dehydrogenation Reactor | Pressure of Oligomerization Reactor | $C_{2+}$ Concentration in $CH_4$-rich Stream | Overall $C_{2+}$ Loss | Overall Liquid Hydrocarbon Yield |
|---|---|---|---|---|---|---|
| Comp. Simulation 1 | 3 | 5 bar | 29 bar | 11.08% | 20.32% | 79.68% |
| Comp. Simulation 2 | 3 | 29 bar | 29 bar | 18.44% | 36.88% | 63.12% |
| Simulation 3 | 5 | 29 bar | 29 bar | 2.45% | 4.2% | 95.8% |
| Simulation 4 | 6 | 29 bar | 29 bar | 1.67% | 2.8% | 97.2% |

TABLE 4

Major Stream Information for Simulation 1 (all concentrations are reported as mol %).

| | Sweet and dry shale gas 30 | $CH_4$-rich stream 39 | Flash Drum 312 Feed 34 | Flash Drum 312 Gas Out 32 | Flash Drum 312 Liquid Out 31 | Recycle stream 303 | Liquid Product 33 |
|---|---|---|---|---|---|---|---|
| Temperature (° C.) | 50 | 25 | −20 | −20 | −20 | 22 | 22 |
| Pressure (bar) | 28.62 | 29.27 | 29.48 | 29.27 | 29.27 | 1.19 | 1.19 |
| Flowrate (kmol/h) | 4609.38 | 3213.02 | 5940.82 | 4063.43 | 1337.39 | 1597.31 | 544.84 |
| $N_2$ | 1.64 | 2.35 | 1.29 | 1.64 | 0.09 | 0.12 | 0.00 |
| $H_2$ | 0.00 | 0.00 | 23.59 | 30.20 | 0.83 | 0.93 | 0.00 |
| $CH_4$ | 60.36 | 86.57 | 49.71 | 60.42 | 12.83 | 17.00 | 0.14 |
| $C_2H_6$ | 20.86 | 7.03 | 5.71 | 4.91 | 8.49 | 23.36 | 0.57 |
| $C_3H_8$ | 11.85 | 0.48 | 8.24 | 0.33 | 2.51 | 8.97 | 0.57 |
| $C_4H_{10}$ | 3.96 | 0.66 | 2.78 | 0.47 | 10.72 | 16.81 | 5.63 |
| $C_{5+}$ alkanes | 1.34 | 0.07 | 1.71 | 0.05 | 5.04 | 6.10 | 10.96 |
| $C_2H_4$ | 0.00 | 0.17 | 0.12 | 0.12 | 0.13 | 0.15 | 0.00 |
| $C_3H_6$ | 0.00 | 1.90 | 2.93 | 1.33 | 8.44 | 8.02 | 1.67 |
| $C_4H_8$ | 0.00 | 0.41 | 2.79 | 0.41 | 10.96 | 8.65 | 6.32 |
| $C_{5+}$ alkenes | 0.00 | 0.03 | 1.13 | 0.12 | 39.96 | 9.89 | 74.14 |

TABLE 5

Major Stream Information for Simulation 2 (all concentrations are reported as mol %).

| | Sweet and dry shale gas 30 | $CH_4$-rich stream 39 | Flash Drum 312 Feed 34 | Flash Drum 312 Gas Out 32 | Flash Drum 312 Liquid Out 31 | Recycle stream 303 | Liquid Product 33 |
|---|---|---|---|---|---|---|---|
| Temperature (° C.) | 50 | 25 | −20 | −20 | −20 | 22 | 22 |
| Pressure (bar) | 28.62 | 29.27 | 29.48 | 29.27 | 29.27 | 1.19 | 1.19 |
| Flowrate (kmol/h) | 4609.38 | 3502.97 | 6626.13 | 4580.75 | 2045.38 | 792.55 | 448.07 |
| $N_2$ | 1.64 | 2.15 | 1.17 | 1.64 | 0.10 | 0.16 | 0.00 |
| $H_2$ | 0.00 | 0.00 | 16.49 | 23.53 | 0.72 | 1.40 | 0.00 |
| $CH_4$ | 60.36 | 79.41 | 46.09 | 60.73 | 13.30 | 21.54 | 0.11 |
| $C_2H_6$ | 20.86 | 14.12 | 13.16 | 10.80 | 18.45 | 13.93 | 0.95 |
| $C_3H_8$ | 11.85 | 1.32 | 2.95 | 1.01 | 7.30 | 3.85 | 1.33 |
| $C_4H_{10}$ | 3.96 | 0.85 | 4.97 | 0.65 | 14.67 | 14.22 | 6.99 |
| $C_{5+}$ alkanes | 1.34 | 0.08 | 2.41 | 0.06 | 7.63 | 5.04 | 13.08 |

TABLE 5-continued

Major Stream Information for Simulation 2 (all concentrations are reported as mol %).

| | Sweet and dry shale gas 30 | CH$_4$-rich stream 39 | Flash Drum 312 Feed 34 | Flash Drum 312 Gas Out 32 | Flash Drum 312 Liquid Out 31 | Recycle stream 303 | Liquid Product 33 |
|---|---|---|---|---|---|---|---|
| C$_2$H$_4$ | 0.00 | 0.15 | 0.12 | 0.11 | 0.12 | 0.21 | 0.00 |
| C$_3$H$_6$ | 0.00 | 1.40 | 2.74 | 1.07 | 6.48 | 13.09 | 1.02 |
| C$_4$H$_8$ | 0.00 | 0.40 | 2.56 | 0.31 | 7.60 | 14.15 | 3.84 |
| C$_{5+}$ alkenes | 0.00 | 0.12 | 6.9 | 0.02 | 23.63 | 12.41 | 72.68 |

TABLE 6

Major Stream Information for Simulation 3 (all concentrations are reported as mol %).

| | Sweet and dry shale gas 50 | CH$_4$-rich stream 59 | Absorption Tower 512 Feed 54 | Absorption Tower 512 Gas Out 52 | Absorption Tower 512 Liquid Out 51 | Recycle stream 503 | Liquid Product 53 |
|---|---|---|---|---|---|---|---|
| Temperature (° C.) | 35 | 25 | −20 | −16 | −11 | 23 | 23 |
| Pressure (bar) | 28.41 | 29.48 | 29.48 | 29.27 | 29.48 | 1.19 | 1.19 |
| Flowrate (kmol/h) | 4609.38 | 2928.24 | 10449 | 4511.61 | 11208 | 5351.71 | 576.55 |
| N$_2$ | 1.64 | 2.57 | 0.80 | 1.67 | 0.07 | 0.15 | 0.00 |
| H$_2$ | 0.00 | 0.00 | 15.93 | 35.10 | 0.72 | 1.51 | 0.00 |
| CH$_4$ | 60.36 | 94.98 | 38.10 | 61.65 | 10.77 | 22.40 | 0.15 |
| C$_2$H$_6$ | 20.86 | 1.28 | 16.03 | 0.83 | 15.19 | 30.46 | 1.23 |
| C$_3$H$_8$ | 11.85 | 0.14 | 2.43 | 0.09 | 2.55 | 4.59 | 0.67 |
| C$_4$H$_{10}$ | 3.96 | 0.46 | 9.61 | 0.30 | 12.09 | 17.75 | 6.92 |
| C$_{5+}$ alkanes | 1.34 | 0.09 | 2.70 | 0.06 | 5.88 | 2.77 | 10.02 |
| C$_2$H$_4$ | 0.00 | 0.03 | 0.13 | 0.02 | 0.11 | 0.23 | 0.00 |
| C$_3$H$_6$ | 0.00 | 0.17 | 2.98 | 0.11 | 3.06 | 5.64 | 0.70 |
| C$_4$H$_8$ | 0.00 | 0.13 | 2.79 | 0.08 | 3.62 | 5.14 | 2.24 |
| C$_{5+}$ alkenes | 0.00 | 0.15 | 8.5 | 0.09 | 45.94 | 9.36 | 78.07 |

TABLE 7

Major Stream Information for Simulation 4 (all concentrations are reported as mol %).

| | Sweet and dry shale gas 60 | CH$_4$-rich stream 69 | Absorption Tower 612 Feed 64 | Absorption Tower 612 Gas Out 62 | Absorption Tower 612 Liquid Out 61 | Recycle stream 603 | Liquid Product 63 |
|---|---|---|---|---|---|---|---|
| Temperature (° C.) | 35 | 25 | −10 | −6 | 0 | 77 | 243 |
| Pressure (bar) | 28.41 | 29.48 | 29.48 | 29.27 | 29.48 | 29.48 | 29.48 |
| Flowrate (kmol/h) | 4609.38 | 2905.87 | 11160.48 | 4511.61 | 12291.72 | 6000.00 | 629.17 |
| N$_2$ | 1.64 | 2.59 | 0.75 | 1.67 | 0.07 | 0.16 | 0.00 |
| H$_2$ | 0.00 | 0.00 | 15.40 | 35.87 | 0.71 | 1.56 | 0.00 |
| CH$_4$ | 60.36 | 95.74 | 35.30 | 61.40 | 9.42 | 19.30 | 0.00 |
| C$_2$H$_6$ | 20.86 | 0.42 | 15.35 | 0.27 | 13.86 | 28.35 | 0.04 |
| C$_3$H$_8$ | 11.85 | 0.02 | 2.24 | 0.01 | 2.06 | 4.14 | 0.08 |
| C$_4$H$_{10}$ | 3.96 | 0.54 | 17.89 | 0.34 | 19.53 | 34.09 | 5.65 |
| C$_{5+}$ alkanes | 1.34 | 0.12 | 0.98 | 0.08 | 5.02 | 0.92 | 9.16 |
| C$_2$H$_4$ | 0.00 | 0.04 | 0.11 | 0.03 | 0.09 | 0.19 | 0.00 |
| C$_3$H$_6$ | 0.00 | 0.02 | 2.61 | 0.01 | 2.39 | 4.83 | 0.07 |
| C$_4$H$_8$ | 0.00 | 0.44 | 2.35 | 0.05 | 44.32 | 4.23 | 0.91 |
| C$_{5+}$ alkenes | 0.00 | 0.07 | 7.02 | 0.27 | 2.53 | 2.23 | 84.09 |

The present invention further includes any one or more of the following embodiments:

1. A process for upgrading natural gas liquids (NGL), comprising:
providing a processed sweet and dry shale gas stream where the acid gas and water concentrations are within the desired range for downstream processing;
processing the sweet and dry shale gas to convert C2+ hydrocarbon to liquid hydrocarbon stream; and
at least a portion of the liquid hydrocarbon product is used as the absorbent for $CH_4$ recovery.

2. A process for upgrading natural gas liquids (NGL), comprising:
providing a processed sweet and dry shale gas stream where the acid gas and water concentrations are within the desired range for downstream processing;
processing the sweet and dry shale gas to convert C2+ hydrocarbon to liquid hydrocarbon stream; and
at least a portion of the liquid hydrocarbon product is used as the absorbent for CH4 and H2 recovery.

3. The process according to embodiments 1 or 2, wherein processing the sweet and dry shale gas to liquid hydrocarbon stream comprises a dehydrogenation step followed by an oligomerization step.

4. The process according to embodiment 3, wherein the dehydrogenation reaction and the oligomerization reaction take place before the separation between CH4 and C2+.

5. The process according to any embodiment 1 to 4, wherein a membrane is used to separate CH4 and H2.

6. The process according to any embodiment 1 to 5, further comprising absorbing unconverted C2+ hydrocarbons from the sweet and dry shale gas using a recycled liquid stream and further separating the effluent into a liquid hydrocarbon stream and a stream containing NGLs and alkene derivatives using a flash drum.

7. The process according to any embodiment 1 to 6, further comprising absorbing unconverted C2+ hydrocarbons from the sweet and dry shale gas using a recycled liquid stream and further separating the effluent into a liquid hydrocarbon stream and a stream containing NGLs and alkene derivatives using a distillation column.

8. The process according to any embodiment 3 to 7, wherein the dehydrogenation reaction and the oligomerization reaction take place after the separation between CH4 and C2+ and before the separation between H2 and C2+.

9. The process according to any embodiment 6 to 8, wherein the liquid streams from two absorption towers are mixed together and separated into a liquid hydrocarbon stream and a stream containing NGLs and their alkene derivatives through a flash drum.

10. The process according to any embodiment 6 to 9, wherein the liquid streams from two absorption towers are mixed together and separated into a liquid hydrocarbon stream and a stream containing NGLs and their alkene derivatives through a distillation column.

11. The process according to any embodiment 3 to 10, wherein the separation between CH4 (or H2) and C2+ takes place between the dehydrogenation reaction and the oligomerization reaction.

12. The process according to embodiment 11, wherein a membrane is used to separate CH4 and H2.

13. The process according to any embodiment 3 to 12, wherein the product from the oligomerization reaction is separated into a liquid hydrocarbon stream and a stream containing NGLs and their alkene derivatives through a flash drum.

14. The process according to any embodiment 3 to 13, wherein the product from the oligomerization reaction is separated into a liquid hydrocarbon stream and a stream containing NGLs and their alkene derivatives through a distillation column.

15. The process according to any embodiment 1 to 14, wherein the process to upgrade the sweet and dry shale gas to liquid hydrocarbon stream is a reaction sequence comprising a dehydrogenation reaction, an oligomerization reaction and a hydrogenation reaction.

16. The process according to embodiment 15, wherein the reaction sequence takes place before the separation between CH4 (or H2) and C2+.

17. The process according to embodiment 16, wherein a membrane is used to separate CH4 and H2.

18. The process according to any embodiment 3 to 17, wherein the liquid stream from an absorption tower is separated into a liquid hydrocarbon stream and a stream containing NGLs and their alkene derivatives through a flash drum.

19. The process according to any embodiment 3 to 18, wherein the liquid stream from an absorption tower is separated into a liquid hydrocarbon stream and a stream containing NGLs and their alkene derivatives through a distillation column.

20. The process according to any embodiment 15 to 19, wherein the sequence of reactions takes place after the separation between CH4 and C2+.

21. The process according to embodiment 20, wherein liquid streams from two absorption towers are mixed together and separated into a liquid hydrocarbon stream and a stream containing NGLs and their alkene derivatives using a flash drum.

22. The process according to any embodiment 20 to 21, wherein liquid streams from two absorption towers are mixed together and separated into a liquid hydrocarbon stream and a stream containing NGLs and their alkene derivatives using a distillation column.

23. The process according to any embodiment 15 to 23, wherein the separation between CH4 (or H2) and C2+ takes place between the dehydrogenation reaction and the oligomerization reaction.

24. The process according to any embodiment 1 to 23, wherein a portion of a H2-rich stream is fed to a hydrogenation reactor.

25. The process according to any embodiment 1 to 24, wherein a membrane is used to separate CH4 and H2.

26. The process according to any embodiment 24 to 25, wherein the product stream from the hydrogenation reactor is separated into a liquid hydrocarbon stream and a stream containing NGLs and their alkene derivatives through a flash drum.

27. The process according to any embodiment 24 to 26, wherein the product stream from the hydrogenation reactor is separated into a liquid hydrocarbon stream and a stream containing NGLs and their alkene derivatives through a distillation column.

28. The process according to embodiments 1 to 27, wherein a hydrogenation reaction takes place after the liquid hydrocarbon stream is recovered.

29. The process according to any embodiment 24 to 28, wherein the $H_2$-rich stream is fed to the hydrogenation reactor.

30. The process according to any embodiment 1 to 29, wherein a membrane is used to separate CH4 and H2.

31. The process according to any embodiment 26 to 29, wherein the liquid stream from an absorption tower is separated into a liquid hydrocarbon stream and a stream containing NGLs and their alkene derivatives using a flash drum.

32. The process according to any embodiment 26 to 29, wherein the liquid stream from an absorption tower is separated into a liquid hydrocarbon stream and a stream containing NGLs and their alkene derivatives using a distillation column.

33. The process according to any embodiment 26 to 32, wherein a hydrogenation reaction takes place after the liquid hydrocarbon stream is recovered.

34. The process according to any embodiment 24 to 33, wherein the H2-rich stream is fed to the hydrogenation reactor.

35. The process according to any embodiment 26 to 34, wherein the liquid stream from the two absorption towers are mixed together and separated into a liquid hydrocarbon stream and a stream containing NGLs and their alkene derivatives through a flash drum.

36. The process according to any embodiment 26 to 35, wherein the liquid streams from the two absorption towers are mixed together and separated into a liquid hydrocarbon stream and a stream containing NGLs and their alkene derivatives through a distillation column.

37. The process according to any embodiment 26 to 36, wherein there is a hydrogenation reaction takes place after the liquid hydrocarbon stream is recovered.

38. The process according to any embodiment 24 to 37, wherein the H2-rich stream is fed to the hydrogenation reactor.

39. The process according to any embodiment 26 to 38, a membrane is used to separate CH4 and H2 streams.

40. The process according to any embodiment 26 to 39, wherein the product stream from the oligomerization reactor is separated into a liquid hydrocarbon stream and a stream containing NGLs and their alkene derivatives through a flash drum.

41. The process according to any embodiment 26 to 40, wherein the product stream from the oligomerization reactor is separated into a liquid hydrocarbon stream and a stream containing NGLs and their alkene derivatives through a distillation column.

42. The process according to any embodiment 1 to 41, wherein the process to upgrade the sweet and dry shale gas to liquid hydrocarbon is a reaction sequence of a dehydrogenation reaction, a membrane separation, an oligomerization reaction and a hydrogenation reaction.

43. The process according to embodiments 41 or 42, wherein the reaction sequence takes place before the separation of CH4 and C2+.

44. The process according to any embodiment 41 to 43, wherein a membrane is used to separate CH4 and H2.

45. The process according to any embodiment 41 to 44, wherein the liquid stream from an absorption tower is separated into a liquid hydrocarbon stream and a stream containing NGLs and their alkene derivatives through a flash drum.

46. The process according to any embodiment 41 to 45, wherein the liquid stream from an absorption tower is separated into a liquid hydrocarbon stream and a stream containing NGLs and their alkene derivatives through a distillation column.

47. The process according to any embodiment 41 to 46, wherein the sequence of reactions takes place after the separation between CH4 and C2+.

48. The process according to any embodiment 41 to 47, wherein the liquid streams from the two absorption towers are mixed together and separated into a liquid hydrocarbon stream and a stream containing NGLs and their alkene derivatives through a flash drum.

49. The process according to any embodiment 41 to 48, wherein the liquid streams from the two absorption towers are mixed together and separated into a liquid hydrocarbon stream and a stream containing NGLs and their alkene derivatives through a distillation column.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, meaning the values take into account experimental error, machine tolerances and other variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:

1. A process for upgrading natural gas liquids (NGL), comprising:
    a) providing a natural gas comprising methane and one or more natural gas liquids;
    b) converting at least a portion of the natural gas liquids to one or more liquid hydrocarbons;
    c) separating the methane from the one or more liquid hydrocarbons using a liquid absorbent to provide a first separated stream comprising the methane from the converted stream and a second separated stream comprising the one or more liquid hydrocarbons from the converted stream; and
    d) recycling at least a portion of the one or more liquid hydrocarbons as the liquid absorbent.

2. The process of claim 1, wherein the one or more liquid hydrocarbons comprises C2+ alkenes.

3. The process of claim 1, wherein the one or more liquid hydrocarbons comprises C2+ alkenes derived from the dehydrogenation of the natural gas liquids.

4. The process of claim 3, wherein the one or more liquid hydrocarbons comprises one or more C4 to C26 oligomers derived from the oligomerization of the C2+ alkenes.

5. The process of claim 1, wherein the natural gas is derived from shale gas.

6. The process of claim 1, wherein the natural gas is a sweet and dry natural gas.

7. The process of claim 1, wherein converting at least a portion of the natural gas liquids to one or more liquid hydrocarbons comprises dehydrogenating any C2+ hydrocarbons in the natural gas to provide one or more C2+ olefins and then oligomerizing the one or more C2+ olefins to provide one or more 4 to C26 oligomers.

8. The process of claim 7, wherein separating the methane from the one or more liquid hydrocarbons using a liquid absorbent occurs after the dehydrogenation and the oligomerization.

9. The process of claim 7, wherein separating the methane from the one or more liquid hydrocarbons using a liquid absorbent occurs before the dehydrogenation and the oligomerization.

10. The process of claim 7, wherein separating the methane from the one or more liquid hydrocarbons using a liquid absorbent occurs after the dehydrogenation and before the oligomerization.

11. The process of claim 10, wherein the second separated stream is further separated into a light hydrocarbon gas stream that is recycled for dehydrogenation and a concentrated liquid product stream.

12. The process of claim 11, wherein the second separated stream is separated using a flash drum.

13. The process of claim 11, wherein the second separated stream is separated using a distillation column.

14. The process of claim 11, wherein at least a portion of the concentrated liquid product stream is recycled as the absorbent.

15. A process for upgrading natural gas liquids (NGL), comprising:
   a) providing a natural gas comprising methane and one or more $C_{2+}$ hydrocarbons;
   b) dehydrogenating at least a portion of the one or more $C_{2+}$ hydrocarbons into one or more $C_{2+}$ olefinic hydrocarbons to provide a first converted stream comprising methane and the one or more $C_{2+}$ olefinic hydrocarbons;
   c) oligomerizing the first converted stream to provide a second converted stream comprising methane and one or more C4 to C26 oligomers;
   d) separating the methane from the second converted stream using a liquid absorbent to provide a first separated stream comprising the methane from the second converted stream and a second separated stream comprising the one or more C4 to C26 oligomers from the second converted stream; and
   e) recycling at least a portion of the one or more C4 to C26 oligomers as the liquid absorbent.

16. The process of claim 15, further comprising separating hydrogen from the first separated stream.

17. The process of claim 15, further comprising separating hydrogen from the second converted stream using the absorbent.

18. The process of claim 1, wherein the natural gas is derived from shale gas.

19. The process of claim 1, wherein the natural gas is a sweet and dry natural gas.

20. A process for upgrading natural gas liquids (NGL), comprising:
   a) providing a sweet and dry shale gas comprising at least 50 mol % methane and 5 mol % to 40 mol % one or more $C_{2+}$ paraffins;
   b) dehydrogenating at least a portion of the one or more $C_{2+}$ paraffins into one or more $C_{2+}$ olefins to provide a first converted stream comprising methane and the one or more $C_{2+}$ olefins;
   c) oligomerizing the first converted stream to provide a second converted stream comprising methane and one or more C4 to C26 oligomers;
   d) absorbing the methane from the second converted stream using a liquid absorbent to provide a first separated stream comprising the methane from the second converted stream and a second separated stream comprising the one or more C4 to C26 oligomers from the second converted stream;
   e) separating hydrogen from the methane in the first separated stream;
   f) separating gas from the one or more C4 to C26 oligomers in the second separated stream to provide an oligomer product comprising the one or more C4 to C26 oligomers; and
   g) recycling at least a portion of the oligomer product as the liquid absorbent.

* * * * *